US012673037B2

(12) United States Patent
Milner et al.

(10) Patent No.: US 12,673,037 B2
(45) **Date of Patent: *Jul. 7, 2026**

(54) METHODS OF TREATING AMYOTROPHIC LATERAL SCLEROSIS

(71) Applicant: BioJiva LLC, Los Altos, CA (US)

(72) Inventors: Peter Milner, Los Altos, CA (US); Mikhail Sergeevich Shchepinov, Kingston Upon Thames (GB)

(73) Assignee: BioJiva LLC, San Jose, CA (US)

( * ) Notice: Subject to any disclaimer, the term of this patent is extended or adjusted under 35 U.S.C. 154(b) by 899 days.

This patent is subject to a terminal disclaimer.

(21) Appl. No.: 17/949,713

(22) Filed: Sep. 21, 2022

(65) Prior Publication Data

US 2023/0255917 A1 Aug. 17, 2023

Related U.S. Application Data

(63) Continuation of application No. 17/391,909, filed on Aug. 2, 2021, now Pat. No. 11,491,130, which is a continuation-in-part of application No. 17/169,271, filed on Feb. 5, 2021, now Pat. No. 11,351,143.

(51) Int. Cl.
*A61K 31/202* (2006.01)
*A61K 31/232* (2006.01)
*A61P 25/28* (2006.01)

(52) U.S. Cl.
CPC .......... *A61K 31/202* (2013.01); *A61K 31/232* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 1,166,930 A | 1/1916 | Shchepinov | |
| 2,798,053 A | 7/1957 | Brown | |
| 3,520,872 A | 7/1970 | Wechter | |
| 3,755,560 A | 8/1973 | Dickert et al. | |
| 4,421,769 A | 12/1983 | Dixon et al. | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,011,681 A | 4/1991 | Ciotti et al. | |
| 5,087,445 A | 2/1992 | Haffey et al. | |
| 5,100,660 A | 3/1992 | Hawe et al. | |
| 5,194,448 A | 3/1993 | Coupland et al. | |
| 5,436,269 A | 7/1995 | Yazawa et al. | |
| 5,709,888 A | 1/1998 | Gil et al. | |
| 5,843,497 A | 12/1998 | Sundram et al. | |
| 5,914,347 A | 6/1999 | Grinda | |
| 6,111,066 A | 8/2000 | Anderson, III et al. | |
| 6,331,532 B1 | 12/2001 | Murphy et al. | |
| 6,417,233 B1 | 7/2002 | Sears et al. | |
| 6,503,478 B2 | 1/2003 | Chaiken et al. | |
| 7,179,928 B2 | 2/2007 | Smith et al. | |
| 7,232,809 B2 | 6/2007 | Murphy et al. | |
| 7,432,305 B2 | 10/2008 | Miller et al. | |
| 7,470,798 B2 | 12/2008 | Wang et al. | |
| 7,514,461 B2 | 4/2009 | Wang et al. | |
| 7,888,334 B2 | 2/2011 | Murphy et al. | |
| 7,888,335 B2 | 2/2011 | Taylor et al. | |
| 10,052,299 B2 | 8/2018 | Shchepinov | |
| 10,058,522 B2 | 8/2018 | Shchepinov | |
| 10,058,612 B2 | 8/2018 | Shchepinov | |
| 10,154,983 B2 | 12/2018 | Shchepinov | |
| 10,730,821 B2 | 8/2020 | Vidovic et al. | |
| 11,351,143 B1 * | 6/2022 | Milner | A61K 31/232 |
| 11,491,130 B2 * | 11/2022 | Milner | A61K 31/201 |
| 2001/0023259 A1 | 9/2001 | Slabas et al. | |
| 2002/0052342 A1 | 5/2002 | Murphy et al. | |
| 2002/0081689 A1 | 6/2002 | Yan et al. | |
| 2002/0198177 A1 | 12/2002 | Horrobin | |
| 2003/0032078 A1 | 2/2003 | Travis | |
| 2003/0069208 A1 | 4/2003 | Murphy et al. | |
| 2004/0043013 A1 | 3/2004 | McCleary | |
| 2004/0106579 A1 | 6/2004 | Murphy et al. | |
| 2005/0043553 A1 | 2/2005 | Smith et al. | |
| 2005/0164908 A1 | 7/2005 | Ginsberg et al. | |
| 2005/0245487 A1 | 11/2005 | Murphy et al. | |
| 2006/0035382 A1 | 2/2006 | Shinozaki et al. | |
| 2006/0205685 A1 | 9/2006 | Phiasivongsa et al. | |
| 2006/0229278 A1 | 10/2006 | Taylor et al. | |

(Continued)

FOREIGN PATENT DOCUMENTS

| | | | |
|---|---|---|---|
| CN | 1114878 A | 1/1996 |
| EP | 0713653 A1 | 5/1996 |

(Continued)

OTHER PUBLICATIONS

Non-Final Office Action issued in U.S. Appl. No. 16/997,692, mailed on Feb. 4, 2022.
Brenna, J. Thomas et al. (2020, e-published Aug. 29, 2020). "Plasma and Red Blood Cell Membrane Accretion and Pharmacokinetics of RTOO1 (bis-Allylic 11, 11-D2-Linoleic Acid Ethyl Ester) during Long Term Dosing in Patients." Journal of Pharmaceutical Sciences, 109(11 ), 3496-3503. https://doi.org/10.1016/j.xphs.2020.08.019.
International Search Report, PCT/US 22/15366, filed on Feb. 4, 2022, date of mailing of the ISR Jul. 1, 2022.
Adams et al.: Case Report: Expanded Access Treatment of an Infantile Neuroaxonal Dystrophy (INAD) Patient with a Novel, Stabilized Polyunsaturated Fatty Acid Drug, American Academy of Neurology conference, poster session, Apr. 2018.

(Continued)

*Primary Examiner* — Jeffrey S Lundgren
*Assistant Examiner* — Michael J Schmitt
(74) *Attorney, Agent, or Firm* — Young Basile Hanlon & MacFarlane, P.C.

(57) ABSTRACT

Disclosed are methods for inhibiting the progression of neurodegenerative disease. The methods include administering to a patient suffering from such a disease a composition comprising either deuterated linoleic acid or an ester thereof.

11 Claims, 1 Drawing Sheet

(56) References Cited

U.S. PATENT DOCUMENTS

| | | | |
|---|---|---|---|
| 2006/0241088 | A1 | 10/2006 | Arterburn et al. |
| 2007/0004639 | A1 | 1/2007 | Kane et al. |
| 2007/0032548 | A1 | 2/2007 | Ellis |
| 2007/0238709 | A1 | 10/2007 | Murphy et al. |
| 2007/0270381 | A1 | 11/2007 | Murphy et al. |
| 2008/0161267 | A1 | 7/2008 | Taylor et al. |
| 2008/0234197 | A1 | 9/2008 | Allam et al. |
| 2008/0275005 | A1 | 11/2008 | Murphy et al. |
| 2009/0054504 | A1 | 2/2009 | Bozik et al. |
| 2009/0069354 | A1 | 3/2009 | Czarnik |
| 2009/0181367 | A1 | 7/2009 | Cote et al. |
| 2009/0182022 | A1 | 7/2009 | Rongen et al. |
| 2009/0215896 | A1 | 8/2009 | Morseman et al. |
| 2009/0232916 | A1 | 9/2009 | Shulman et al. |
| 2009/0258841 | A1 | 10/2009 | Murphy et al. |
| 2009/0280516 | A1 | 11/2009 | Chen et al. |
| 2009/0306015 | A1 | 12/2009 | Gately et al. |
| 2009/0326070 | A1 | 12/2009 | Freeman et al. |
| 2010/0022645 | A1 | 1/2010 | Nelson et al. |
| 2010/0029706 | A1 | 2/2010 | Miller et al. |
| 2010/0056643 | A1 | 3/2010 | Bachynsky et al. |
| 2010/0160248 | A1 | 6/2010 | Shchepinov |
| 2010/0168051 | A1 | 7/2010 | Malik |
| 2011/0028434 | A1 | 2/2011 | Destaillats et al. |
| 2011/0028493 | A1 | 2/2011 | Matsunaga et al. |
| 2011/0046219 | A1 | 2/2011 | Hlinman et al. |
| 2011/0082206 | A1 | 4/2011 | Miller |
| 2011/0092592 | A1 | 4/2011 | Yano |
| 2011/0105609 | A1 | 5/2011 | Shchepinov |
| 2011/0144051 | A1 | 6/2011 | Von Borstel |
| 2011/0189212 | A1 | 8/2011 | Harats et al. |
| 2011/0190195 | A1 | 8/2011 | Atlas |
| 2012/0005765 | A1 | 1/2012 | Kumar et al. |
| 2013/0309330 | A1 | 11/2013 | Mastronardi |
| 2014/0044692 | A1 | 2/2014 | Shchepinov |
| 2014/0044693 | A1 | 2/2014 | Shchepnov |
| 2014/0050712 | A1 | 2/2014 | Shchepinov |
| 2014/0099648 | A1 | 4/2014 | Walker et al. |
| 2014/0147428 | A1 | 5/2014 | Shchepinov |
| 2016/0303150 | A1 | 10/2016 | Megiddo |
| 2018/0318261 | A1 | 11/2018 | Yang et al. |
| 2019/0046491 | A1 | 2/2019 | Shchepinov |
| 2019/0046644 | A1 | 2/2019 | Shchepinov |
| 2019/0054052 | A1 | 2/2019 | Shchepinov |
| 2019/0231733 | A1 | 8/2019 | Shchepinov |
| 2019/0282529 | A1 | 9/2019 | Shchepinov |
| 2021/0069144 | A1 | 3/2021 | Shchepinov |
| 2021/0186990 | A1 | 6/2021 | Cohen et al. |
| 2021/0244637 | A1 | 8/2021 | Shchepinov |
| 2021/0251933 | A1 | 8/2021 | Shchepinov |
| 2022/0009950 | A1 | 1/2022 | Shchepinov |

FOREIGN PATENT DOCUMENTS

| | | | |
|---|---|---|---|
| EP | 1548116 | A1 | 6/2005 |
| EP | 1834639 | A1 | 9/2007 |
| EP | 1961311 | A1 | 8/2008 |
| EP | 2641891 | A1 | 9/2013 |
| FR | 2721518 | A3 | 12/1995 |
| JP | H02237919 | A | 9/1990 |
| JP | H08268885 | A | 10/1996 |
| JP | H09143492 | A | 6/1997 |
| JP | H10291955 | A | 11/1998 |
| JP | 2000290291 | A | 10/2000 |
| JP | 2001145880 | A | 5/2001 |
| JP | 2001514239 | A | 9/2001 |
| JP | 2001270832 | A | 10/2001 |
| JP | 2001519355 | A | 10/2001 |
| JP | 2002513911 | A | 5/2002 |
| JP | 2002527387 | A | 8/2002 |
| JP | 2002536981 | A | 11/2002 |
| JP | 2004081156 | A | 3/2004 |
| JP | 2004520848 | A | 7/2004 |
| JP | 2004530635 | A | 10/2004 |
| JP | 2005510501 | A | 4/2005 |
| JP | 2006502081 | A | 1/2006 |
| JP | 2006504701 | A | 2/2006 |
| JP | 2006510669 | A | 3/2006 |
| JP | 2008504372 | A | 2/2008 |
| JP | 2009007337 | A | 1/2009 |
| JP | 2009502745 | A | 1/2009 |
| JP | 2009525948 | A | 7/2009 |
| JP | 2010521493 | A | 6/2010 |
| JP | 2013509439 | A | 3/2013 |
| JP | 2013189437 | A | 9/2013 |
| JP | 2014502974 | A | 2/2014 |
| JP | 2016138138 | A | 8/2016 |
| KR | 20050029582 | A | 3/2005 |
| WO | 9956790 | A2 | 11/1999 |
| WO | 0021524 | A1 | 4/2000 |
| WO | 0117374 | A1 | 3/2001 |
| WO | 02096221 | A2 | 12/2002 |
| WO | 03035095 | A1 | 5/2003 |
| WO | 03051348 | A2 | 6/2003 |
| WO | 03064576 | A2 | 8/2003 |
| WO | 2004028536 | A1 | 4/2004 |
| WO | 2004029254 | A1 | 4/2004 |
| WO | 2004052227 | A2 | 6/2004 |
| WO | 2005037848 | A2 | 4/2005 |
| WO | 2007049098 | A2 | 5/2007 |
| WO | 2007102030 | A1 | 9/2007 |
| WO | 2008143642 | A2 | 11/2008 |
| WO | 2009017833 | A2 | 2/2009 |
| WO | 2009097331 | A1 | 8/2009 |
| WO | 2009114809 | A1 | 9/2009 |
| WO | 2009114814 | A2 | 9/2009 |
| WO | 2009123316 | A1 | 10/2009 |
| WO | 2009151125 | A1 | 12/2009 |
| WO | 2010010365 | A1 | 1/2010 |
| WO | 2010014585 | A1 | 2/2010 |
| WO | 2010068867 | A1 | 6/2010 |
| WO | 2010106211 | A1 | 9/2010 |
| WO | 2010132347 | A2 | 11/2010 |
| WO | 2010143053 | A1 | 12/2010 |
| WO | 2011053870 | A1 | 5/2011 |
| WO | 2011097273 | A1 | 8/2011 |
| WO | 2012100347 | A1 | 8/2012 |
| WO | 2012148926 | A2 | 11/2012 |
| WO | 2012148927 | A2 | 11/2012 |
| WO | 2012148929 | A2 | 11/2012 |
| WO | 2012148930 | A2 | 11/2012 |
| WO | 2012174262 | A2 | 12/2012 |
| WO | 2017037567 | A1 | 3/2017 |
| WO | 2017062992 | A1 | 4/2017 |
| WO | 2017091279 | A1 | 6/2017 |
| WO | 2018094116 | A1 | 5/2018 |
| WO | 2019/204582 | A1 | 10/2019 |
| WO | 2019195467 | A1 | 10/2019 |
| WO | 2019241746 | A1 | 12/2019 |
| WO | 2021163186 | A1 | 8/2021 |
| WO | 2021163580 | A1 | 8/2021 |
| WO | 2022170134 | A2 | 8/2022 |
| WO | 2023023397 | A1 | 2/2023 |

OTHER PUBLICATIONS

Adhikary et al.: UVA-visible photo-excitation of guanine radical cations produces sugar radicals in DNA and model structures. Nucleic Acids Research 33(17):5553-5564 (2005).

Angulo et al.: Non-alcoholic fatty liver disease. Journal of Gastroenterology and Hepatology 17 Suppl.:S186-190 (2002).

Asada et al; Stereochemistry of meso-a,e Diaminopimelate Decarboxylase Reaction: The First Evidence for Pyriodoxal 5'-Phosphate Dependant Decarboxylation with Inversion of Configuration. Biochemistry 20(24):6881-6886 (1981).

Bada et al; Isotopic Fractionation During Peptide Bond Hydrolysis. Geochimica et Cosmoschimica Acta 53:3337-3341 (1989).

Balasubramanian et al; DNA strand breaking by the hydroxyl radical is governed by the accessible surface areas of the hydrogen atoms of the DNA backbone. Proc. Natl. Acad. Sci. USA 95:9738-9743 (1998).

(56) References Cited

OTHER PUBLICATIONS

Barber et al.: Oxidative stress in ALS: a mechanism of neurodegeneration and a therapeutic target. Biochimica et Biophysica Acta 1762:1051-1067 (2006).
Brandl et al; The biosynthesis of 3-(trans-2-Nitrocyclopropyl)alanine, a Constituent of the Signal Metabolite Hormaomycin. European Journal of Organic Chemistry 2005(1):123-135 (2004).
Brenna et al; a-Linolenic acid supplementation and conversionton to n-3 long-chain polyunsaturated fatty acids in humans. Prostaglandins, Leukotrienes and Essential Fatty Acids 80:85-91 (2009).
Brenna et al; High-Precision Continuous-Flow Isotope Ratio Mass Spectrometry. Mass Spectrometry Review 16:227-258 (1997).
Brenna, J.T.; Efficiency of conversion of a-linolenic acid to long chain n-3 fatty acids in man. Lipid Metabolism. Curr Opin Clin Nutr Metab Care 5(2):127-132 (2002).
Brenna, J.T.; Use of stable isotopes to study fatty acid and lipoprotein metabolism in man. Prostaglandins, Leukotrienes and Essential Fatty Acids 57(4 & 5):467-472 (1997).
Burdzy et al; Synthesis of stable-isotope enriched 5-methylpyrimidines and their use as probes of base reactivity in DNA. Nucleic Acids Research 30(18):4068-4074 (2002).
Chen et al.: One-Pot Selective Deuteriation of 5'-Dimethoxytritylated Deoxynucleotide Derivatives. Bioorgainc & Medicinal Chemistry Letters 4(6):789-794 (1994).
Chiriac et al; Synthesis of [1,3,6,7-15N, 8-13C] adenine. Journal of Labelled Compounds and Radiopharmaceuticals 42(4):377-385 (1999).
Cho et al; Cooperativity and anti-cooperativity between ligand binding and the dimerization of ristocetin A: asymmetry of a homodimer complex and implications for signal transduction. Chemistry & Biology 3(3):207-215 (1996).
Clarke et al.: Isotope-reinforced polyunsaturated fatty acids protect yeast cells from oxidative stress. FASEB J. 24:849.2 (2010).
Crombie et al, Synthesis of [14,14-2H2]-linolenic acid and its use to confirm the pathway to 12-oxophytodienoic acid (12-oxoPDA) in plants: a conspectus of the epoxycarbonium ion derived family of metabolites from linoleic and inolenic acid hydroperoxides. Journal of the Chemical Society, Perkin Transactions 1(3):581-587 (1991).
Dalle-Donne et al; Protein carbonylation in human diseases. Trends in Molecular Medicine 9(4):169-176 (2003).
Demidov, V.; Heavy isotopes to avert ageing? Trends in Biotechnology 25(9):371-375 (2007).
Dentistry Dictionary reduced-size edition. Oct. 10, 1989, the first edition, p. 2216-2217 (1989).
Dimauro et al.: Mitochondrial respiratory-chain diseases. N Engl J Med. 348(26):2656-2668 (2003).
Duncan et al.: A nonsense mutation in COQ9 causes autosomal-recessive neonatal-onset primary coenzyme Q10 deficiency: a potentially treatable form of mitochondrial disease. The American Journal of Human Genetics 84:558-566 (2009).
Dyall et al, Neurological benefits of Omega-3 Fatty Acids. Neuromolecular Medicine 10(4):219-235 (2008).
Elharram et al.: Deuterium-reinforced polyunsaturated fatty acids improve cognition in a mouse model of sporadic Alzheimer's disease. The FEBS Journal 284(23):4083-4095 (2017).
Emken et al; Effect of Dietary Docosahexaenoic Acid on Desaturation and Uptake in vivo of Isotope-Labeled Oleic, Linoleic, and Linolenic Acids by Male Subjects. Lipids 34(8):785-791 (1999).
Emken et al; Metabolism of cis-12-octadecenoic acid and trans-9, trans-12-octadecadienoic acid and their influence on lipogenic enzyme activities in mouse liver. Biochimica et Biophysica Acta 919:111-121 (1987).
Esaki et al; Synthesis of base-selectively deuterium-labelled nucleosides by the Pd/C-Catalyzed H-D Exchange Reaction in Deuterium Oxide. Heterocycles 66:361-369 (2005).
Evans et al, ENDOR, triple resonance and ESR studies of spin-trapped radicals in autoxidized linoleic acid and its deuterated derivatives. Biochimica et Biophysica Acta, Elsevier Science BV, Amsterdam, NL 835(3):421-425 (1985).
Extended European Search Report for European Application No. 12776294.6 issued on Sep. 25, 2014 by European Patent Office.
Extended European Search Report for European Application No. 12777440 issued on Sep. 17, 2014 by European Patent Office.
Finglas et al, Use of an oral/intravenous dual-label stable-isotope protocol to determine folic acid bioavailability from fortified cereal grain foods in women. The Journal of Nutrition 132(5):936-939 (2002).
Foldesi et al; The Synthesis of Deuterionucleosides; Nucleosides, Nucleotides and Nucleic Acids 19 (10-12):1615-1656 (2000).
Fomich et al.: Full library of (bis-allyl)-deuterated arachidonic acids: synthesis and analytical verification. Chemistry Select 1(15):4758-4764 (2016).
Geboes et al, Validation of a new test meal for a protein digestion breath test in humans. The Journal of Nutrition 134 (4):806-810 (2004).
Giordano, F. J., Oxygen, oxidative stress, hypoxia, and heart failure. The Journal of Clinical Investigation 115 (3):500-508 (2005).
Gueraud et al.: Chemistry and biochemistry of lipid peroxidation products. Free Radical Research 44(10):1098-1124 (2010).
Harman, Deham; The Free Radical Theory of Aging. Antioxidants & Redox Signaling 5(5):557-561 (2003).
Harman, Denham; Aging and Oxidative Stress. Journal of International Federation of Clinical Chemistry (JIFCC) 10(1):24-26 (1998).
Cicalese. Hepatocellular carcinoma. Medscape Reference. 2014;1-5 (2014).
Hill et al. Isotope-reinforced polyunsaturated fatty acids protect yeast cells from oxidative stress. Free Radical Biology & Medicine 50:130-138 (2011).
Hill et al.: Small amounts of isotope-reinforced polyunsaturated fatty acids suppress lipid autoxidation. Free Radical Biology and Medicine 53:893-906 (2012).
Hulme et al; Chemistry and the Worm: Caenorhabditis elegans as a Platform for Integrating Chemical and Biological Research. Chemical Biology; Angewandte Chemie International Edition 50:4774-4807 (2011).
Hussein, N., Long-chain conversion of [13C] linoleic acid and -linoleic acid in response to marked changes in their dietary intake in men. Journal of Lipid Research 46(2):269-280 (2004).
Ikeya et al; Evaluation of stereo-array isotope labeling (SAIL) patterns for automated structural analysis of proteins with CYANA. Magnetic Resonance in Chemistry 44:S152-S157 (2006).
International Search Report and Written Opinion dated Dec. 23, 2010 for PCT/US10/54866.
International Search Report and Written Opinion dated Nov. 29, 2012 for PCT/US2012/034832.
Shah et al.: Resolving the Role of Lipoxygenases in the Initiation and Execution of Ferroptosis, ACS Cent. ScL 4 (3):387-396 (2018).
Shchepinov et al. Isotope effect, essential diet components, and prospects of aging retardation. Russian Journal of General Chemistry 80(7):1514-1522 (2010).
Shchepinov et al.: Mitigating effects of oxidation in aging and diseases. Retrotope. 2010; 1-11 (2010).
Shchepinov, Mikhail; Reactive Oxygen Species, Isotope Effect, Essential Nutrients, and Enhanced Longevity. Rejuvenation Research 10(1):47-59 (2007).
Simpson et al.: Increased lipid peroxidation in sera of ALS patients: a potential biomarker of disease burden. Neurology 62(10):1758-1765 (2004).
Sumbalova et al.: Brain energy metabolsms in experimental chronic diabetes: effect of long-term administration of coenzyme 10 and w-3 polyunsaturated fatty acids. Biologia Bratislava 60(17):105-108 (2005).
Supplementary European Search Report & Written Opinion dated Jun. 5, 2013 for EP Application No. 10827578.5.
Svedruzic et al.; The Mechanism of Target Base Attack in DNA Cytosine Carbon 5 Methylation. Biochemistry 43(36):11460-11473 (2004).
Tang et al; Kinetic and biochemical analysis of the mechanism of action of lysine 5, 6-aminomutase. Archives of Biochemistry and Biophysics 418(1):49-54 (2003).
The extended European search report for European Patent Application No. 12776313 dated Sep. 17, 2014.
Extended European search report for European Patent Application No. 12776521.2 dated Sep. 17, 2014.

(56) References Cited

OTHER PUBLICATIONS

Townend et al.: Dietary Macronutrient Intake and Five-year Incident Cataract: The Blue Mountains Eye Study. American Journal of Ophthalmology, Elsevier, Amsterdam, NL 143(6):932-939 (2007).
Toyama et al; Assignments and hydrogen bond sensitivities of UV resonance Raman bands of the C8-deuterated guanine ring. Journal of Raman Spectroscopy 33(9):699-708 (2002).
Triglycerides. Medium chain triglycerides. Alternative Medicine Review 7(5): 418-420 (2002).
Tucker et al; The synthesis of 11,11-Dideuterolinoleic Acid. Journal of Labelled Compounds 7(1):11-15 (1970).
U.S. Appl. No. 12/916,347 Office Action dated Apr. 6, 2017.
U.S. Appl. No. 12/916,347 Office Action dated Jul. 12, 2013.
U.S. Appl. No. 12/916,347 Office Action dated Nov. 20, 2017.
U.S. Appl. No. 12/916,347 Office Action dated Oct. 22, 2015.
U.S. Appl. No. 16/103,343 Office Action dated Jan. 3, 2020.
U.S. Appl. No. 16/997,692 Notice of Allowance dated Jun. 8, 2022.
U.S. Appl. No. 16/997,692 Office Action dated Feb. 4, 2022.
Veldink et al.: Intake of polyunsaturated fatty acids and vitamin E reduces the risk of developing amyotrophic lateral sclerosis. J Neuro Neurosurg. Psychiatry 78(4):367-371 (2007).
Viswanathan and Cushley, Deuterium Nuclear Magnetic Resonance Study of the Interaction of Substrates and Inhibitors with Soybean Lipoxygenase. The Journal of Biological Chemistry 256(14):7155-7160 (1981).
Wade, David; Deuterium isotope effects on noncovalent interactions between molecules. Chemico-Biological Interactions 117(3):191-217 (1999).
Wendt et al.: Mass spectrometry of perdeuterated molecules of biological origin fatty acid esters from Scenedesmus obliquus. Biochemistry 9(25):4854-4866 (1970).
Wheeler et al.: The Synthesis of the 2H, 3H, and 14C-Isotopomers of 2'-Deoxy-2', 2'-Difourocytidine Hydrochloride, and Anti-Tumor Compound; Journal of Labelled Compounds and Radiopharmaceuticals 29(5):583-589 (1991).
Wilczynska-Kwiatek A et al.: Asthma, allergy, mood disorders, and nutrition. European Journal of Medical research, Biomed Central Ltd. London, UK 14(Suppl 4):248-254 (2009).
Written Opinion dated Sep. 8, 2008 for PCT/GB2007/050112.
Yamauchi et al.: Observation of the Pathway from Lysine to Isoprenoidal Lipid of Halophilic Archaea, Halobacterium halobium and Natrinema pallidum, Using Regiospecifically Deuterated Lysine. Bull. Chem. Soc. Jpn. 74:2199-2205 (2001).
Yashodhara et al., Omega-3 fatty acids: a comprehensive review of their role in health and disease. Postgrad Med J. 85: 84-90 (2009).
Yoneya, et al.: Genetic polymorphisms as risk factors for coronary artery disease. Japanese Journal of Clinical Medicine 56(10):51-56; 2509-2514 (1998).
Zesiewicz et al.: Randomized, Clinical Trial of RT001: Early Signals of Efficacy in Friedreich's Ataxia, Published online Apr. 6, 2018 in Wiley Online Library (wileyonlinelibrary.com). Mov Disord. 33(6):1000-1005 DOI: 10.1002/mds.27353 (2018).
Bieschke et al. Small Molecule Oxidation Products Trigger Disease-Associated Protein Misfolding. Acc. Chem. Res. 2006;39:611-619.
Morris MC. The role of nutrition in Alzheimer's disease: epidemiological evidence. Eur J Neural. 2009; 16(Suppl 1): 1-7.
Australian Government, IP Australia, Examination Report No. 2 for Standard Patent Application, dated May 5, 2017, for Application No. 2012249917.
Australian Government, IP Australia, Notice of Acceptance for Patent Application, dated Jun. 6, 2017 for Application No. 2012249917.
Eiyo Hyoka-to Chiryo [Nutritional assessment and treatment], 2004, vol. 21,No. 3, p. 41 (247)-46(252).
Extended European Search Report dated Jul. 12, 2011 for EP Application No. 09721095.9.
International Search Report and Written Opinion dated Sep. 10, 2010 for PCT/US2009/037173.
International Search Report and Written Opinion dated Jun. 3, 2009 for PCT/US2009/037161.
Office Action dated Apr. 13, 2018 for Canadian Application No. 2,834,274.
Office Action for U.S. Appl. No. 12/916,347 mailed on Sep. 30, 2016.
Office Action for U.S. Appl. No. 14/113,546 mailed on Feb. 22, 2016.
Office Action for U.S. Appl. No. 14/113,546 mailed on Jan. 16, 2015.
Office Action for U.S. Appl. No. 14/113,546 mailed on Jul. 2, 2015.
Office Action for U.S. Appl. No. 14/113,547 mailed on Feb. 19, 2016.
Office Action for U.S. Appl. No. 14/113,547 mailed on Jan. 16, 2015.
Office Action for U.S. Appl. No. 14/113,547 mailed on Jul. 2, 2015.
Office Action for U.S. Appl. No. 14/113,547 mailed on Sep. 16, 2014.
Office Action for U.S. Appl. No. 14/113,553 mailed on Dec. 23, 2014.
Office Action for U.S. Appl. No. 14/113,553 mailed on Jul. 13, 2015.
Office Action for U.S. Appl. No. 14/113,553 mailed on Jun. 2, 2016.
The Journal of the Japanese Society of Internal Medicine, 1992, vol. 81, No. 7, p. 1119(131)-1124(136).
The Merck Manual, 18th ed., in Japanese, 2006, p. 223,224.
Urtti A. Challenges and obstacles of ocular pharmacokinetics and drug delivery, Advanced Drug Delivery Reviews, 2006;58:1131-1135.
Stella et al., Prodrugs: challenges and rewards. vol. 1-2. New York: Published by MPS Press and Springer; 2007.
Christy et al. "Single amino acid polymorphism in aldehyde dehydrogenase gene superfamily," Frontiers in Bioscience, Landmark, 2015, vol. 20, pp. 335-376 (Year: 2015).
International Search Report and Written Opinion received for Application No. PCT/US2017/062107, mailed on Feb. 13, 2018, 13 pages.
Berkowitz et al_ (Dec. 2015) "Measuring In Vivo Free Radical Production by the Outer Retina" Investigative Ophthalmology & Visual Science, 56:7931-7938.
Berkowitz et al. (Feb. 2016) "MRI of Retinal Free Radical Production With Laminar Resolution In Vivo" Investigative Ophthalmology & Visual Science, 57(2):577-585.
D'Souza et al_(Apr. 2015) "Characterization of Aldh2-/-Mice as an Age-related Model of Cognitive Impairment and Alzheimer's Disease" Molecular Brain, 8(27):16 pages.
Fitzmaurice et al. (Dec. 24, 2012) "Aldehyde Dehydrogenase Inhibition as a Pathogenic Mechanism in 5 Parkinson Disease" Proceedings of the National Academy of Sciences of the United States of America, Jan. 8, 2013, e-Published, 110(2):636-641.
Genbank (Aug. 1, 1997) "Aldehyde Dehydrogenase 1 [*Homo sapiens*]" Accession No. AAC51652.1, 2 pages.
Genbank (Mar. 18, 2009) "Aldehyde Dehydrogenase 1 Family, Member A1 [Rattus norvegicus]", Accession No. AAH61526.1, 2 pages.
Genbank (Jul. 15, 2006) "Aldehyde Dehydrogenase 2 Family (Mitochondrial) [*Homo sapiens*)", Accession No. AAH02967.1, 2 pages.
Genbank (Jun. 9, 2008) "Aldehyde Dehydrogenase 3 Family, Member A1 [Rattus norvegicus]" Accession No. AAH70924.1, 2 pages.
Genbank (Aug. 4, 2008) "Aldehyde Dehydrogenase 5 Family, Member A 1 [*Homo sapiens*]" Accession No. AAH34321.1, 2 pages.
Genbank (Jul. 23, 1993) "Aldehyde Dehydrogenase Isozyme 3 [*Homo sapiens*)" Accession No. AAB26658.1, 2 pages.
Genbank (Dec. 12, 2020) "Aldehyde Dehydrogenase X, Mitochondrial Precursor [*Homo sapiens*]" Accession No. NP_000683.3, 3 pages.
Genbank (Dec. 7, 2020) "Aldehyde Dehydrogenase, Dimeric NADP-Preferring Isoform 1 [Mus musculus]" Accession No. NP_001106196.1, 3 pages.
Genbank (Jan. 18, 2021) "Aldehyde Dehydrogenase, Mitochondrial Isoform 1 Precursor [*Homo sapiens*]" Accession No. NP_000681, 4 Pages.

(56) References Cited

OTHER PUBLICATIONS

Genbank (Jan. 18, 2021) "Aldehyde Dehydrogenase, Mitochondrial Isoform 1 Precursor [Mus musculus]" Accession No. NP_033786.1, 4 Pages.
Genbank (Feb. 3, 2021) "Aldehyde Dehydrogenase, Mitochondrial Precursor [Rattus norvegicus)" Accession No. NP_115792.2, 3 pages.
Genbank (Feb. 3, 1997) "mp44a12.r1 Barstead MPLRB1 Mus musculus cDNA clone Image:572062 5' similar to GB:M31690 Mouse argininosuccinate synthease (Mouse), mRNA sequence" Accession No. AA105194.1, 2 pages.
Larson et al. (Aug. 26, 2005) "Disruption of the Coenzyme Binding Site and Dimer Interface Revealed in the 19 Crystal Structure of Mitochondrial Aldehyde Dehydrogenase "Asian" Variant" The Journal of Biological Chemistry, 280: (34) :30550-30556.
Li et al. (Feb. 2006) "Mitochondrial Aldehyde Dehydrogenase-2 {ALDH2) Glu504Lys Polymorphism Contributes to the Variation in Efficacy of Sublingual Nitroglycerin" The Journal of Clinical Investigation, 116:506-511.
Marchitti et al. (Jun. 2007) "Neurotoxicity and Metabolism of the Catecholamine-Derived 3,4-dihydroxyphenylacetaldehyde and 3,4-Dihydroxyphenylglycolaldehyde: The Role of Aldehyde Dehydrogenase" Pharmacological Reviews, 59(2):125-150.
Marchitti et al. (Jun. 2008) "Non-P450 Aldehyde Oxidizing Enzymes: The Aldehyde Dehydrogenase Superfamily" Expert Opinion on Drug Metabolism & Toxicology, 4(6):697-720(37 pages).
McClements et al. {Oct. 2007) "Emulsion-Based Delivery Systems for Lipophilic Bioactive Components" Journal of Food Science, 72(8):R109-R124.
Nema et al. May 9-Jun. 2011. "Excipients and their Role in Approved Injectable Products: Current Usage and Future Directions" PDA Journal of Pharmaceutical Science and Technology, 65(3):287-332.
Porter et al. (Mar. 2007) "Lipids and Lipid-based Formulations: Optimizing the Oral Delivery of Lipophilic Drugs" Nature Reviews Drug Discovery, 6(3):231-248.
Powell et al. (Sep. 1998) "Compendium of Excipients for Parenteral Formulations" PDA Journal of Pharmaceutical Science and Technology, 52(5):238-311.
Shchepinov et al. (2014) "Deuterium Protection of Polyunsaturated Fatty Acids against Lipid Peroxidation: A Novel Approach to Mitigating Mitochondrial Neurological Diseases." Omega-3 Fatty Acids in Brain and Neurological Health, 373-383.
Shchepinov et al. (Aug. 10, 2011) "Isotopic Reinforcement of Essential Polyunsaturated Fatty Acids Diminishes Nigrostriatal Degeneration in a Mouse Model of Parkinson's Disease" Toxicology Letter, 207(2):97-103.
Takeshita et al. (Sep. 1994) "Characterization of the Three Genotypes of Low Km Aldehyde Dehydrogenase in a Japanese Population" Human Genetics, 94(3):217-223.
Wey et al. (Feb. 2012) "Neurodegeneration and Motor Dysfunction in Mice Lacking Cytosolic and Mitochondrial Aldehyde Dehydrogenases: Implications for Parkinson's Disease" PLoS One, 7(2):e31522 (11 pages).
Yu et al. (Nov. 2009) "Characteristics of Aldehyde Dehydrogenase 2 (Aldh2) Knockout Mice" Toxicology Mechanisms and Methods, 19(9):535-540.
Zhang et al. (Oct. 22, 2015) "Impact of Lipid Content on the Ability of Excipient Emulsions to Increase Carotenoid Bioaccessibility from Natural Sources (Raw and Cooked Carrots)" Food Biophysics, 11 :71-80.
Anonymous, (Oct. 3, 2016) "A First in Human Study of RT001 in Patients With Friedreich's Ataxia", ClinicalTrials.gov archive, https://clinicaltrials.gov/ct2/show/NCT02445794.
Fahey et al., (Apr. 2007) "How is Disease Progress in Friedreich's Ataxia Best Measured? A Study of Four Rating Scales", J. Neurol. Neurosurg. Psychiatry, 78(4):411-413.
International Search Report and Written Opinion PCT/US2022/015366 dated Jul. 1, 2022.
International Search Report and Written Opinion received for PCT Application No. PCT/US2022/015535, mailed on Apr. 18, 2022, 9 pages.
Galluzzi et al. (2018) "Molecular Mechanisms of Cell Death: Recommendations of the Nomenclature Committee on Cell Death 2018", Cell Death & Differentiation, 25:486-541.
Gaschler et al. (2017) "Lipid Peroxidation in Cell Death", Biochemical and Biophysical Research Communications, J82(3 ): 419-425.
Non-Final Office Action issued in U.S. Appl. No. 16/997,692, mailed on Feb. 4, 2022, 43 pages.
RT001 in Amyotrophic Lateral Sclerosis, ClinicalTrials.gov NCT04762589, Feb. 21, 2021. 7 pages.
Angelova el al. (Mar. 2018) "Role of Mitochondrial ROS in the Brain: From Physiology to Neurodegeneralion", FEBS Letters, 592:692-702.
Arun et al., (2016)"Mitochondrial Biology and Neurological Diseases", Current Neuropharmacology, 14(2):143-154.
Aufschnalter el al. (Jan. 2017) "Mitochondrial Lipids in Neurodegeneration". Cell and Tissue Research, 367(1):125-140.
Berkers et al. (Jan. 2017) "Topically Applied Fatty Acids are Elongated before Incorporation In the Stratum Comeum Lipid Matrix in Compromised Skin", Experimental Dermatology, 26(1 ):36-43 20 pages.
Buee et al. (1999) "Comparative Biochemistry of Tau in Progressive Supranuclear Palsy, Corticobasal Degeneration, FTDP-17 and Pick's Disease", Brain pathology, 9(4): 681-693.
Cotticeli et al. (Jul. 19, 2013) "Insights Into The Role of Oxidative Stress in the Pathology of Friedreich Ataxia Using Peroxidation Resistant Polyunsaturated Fatty Acids", Redox Biology, 1: 398-404.
Esteras et al. (Sep. 21, 2020} "Mitochondrial Calcium Deregulation in the Mechanism of Beta-Amyloid and Tau Pathology", Cells, 9{2135): 1-17.
Firsov et al. (Mar. 2019) "Threshold Protective Effect of Deuterated Polyunsaturated Fatty Acids on Peroxidation of Lipid Bilayers", The FEBS Journal, 286(11 ): 2099-2117.
Fitzmaurice et al. Sep. 2003 "Nigral glutathione deficiency is not specific for idiopathic Parkinson's disease", Movement Disorders. 18(9): 969-976.
Ganguly et al., (Mar. 16, 2017) "Proteinopathy, Oxidative Stress and Mitochondrial Dysfunction: Cross Talk in Alzheimer's Disease and Parkinson's Disease", Drug Design, Development and Therapy, 11 :797-810.
Gomez-Ramos et al. (2003} "Effect of the Lipid Peroxidation Product Acrolein on Tau Phosphorylation in Neural Cells", Journal of neuroscience research, 71(6):863-870.
Gould Philip L. (Nov. 1986) "Salt Selection For Basic Drugs". International Journal of Pharmaceutics, 33(1-3):201-217.
Lee et al., (Dec. 12, 2018) "The Interface Between ER and Mitochondria: Molecular Compositions and Functions.", Molecules and Cells, 41(12):1000-1007.
Lin et al. (Oct. 2006) "Mitochondrial dysfunction and oxidative stress in neurodegenerative diseases", Nature, 443: 787-795.
Liu et al., (Mar. 15, 2005) "Alzheimer-Specific Epitopes of Tau Represent Lipid Peroxidation-Induced Conformations", Free Radical Biology and Medicine, 38(6):746-754.
Mattson et al. (Dec. 10, 2008) "Mitochondria in Neuroplasticity and Neurological Disorders", Neuron, 60 (5):748-766 (36 Pages.
Murphy et al. (1999) "Mitochondria in Neurodegeneration: Bioenergetic Function in Cell Life and Death", Journal of Cerebral Blood Flow and Metabolism, 19(3): 231-245.
Niki Etsuo (2015) "Lipid Oxidation in the Skin", Free Radical Research, 49(7}:827-834 (34 pages).
Odetti et al. (May 2000) "Lipoperoxidation is Selectively Involved in Progressive Supranuclear Palsy", Journal of Neuropathology & Experimental Neurology, 59(5): 393-397.
Porter NA., (1984) "Chemistry of Lipid Peroxidation", Methods Enzymol, 105:273-282.
Raefsky et al. (2018) "Deuterated Polyunsaturated Fatty Adds Reduce Brain Lipid Peroxidation and Hippocampal Amyloid B-Peptide Levels, Without Discemable Behavioral Effects in an APP/PS 1 Mutant Transgenic Mouse Model of Alzheimer's Disease". Neurobiology of aging, 66:165-176 (31 Pages).

(56) References Cited

OTHER PUBLICATIONS

Zarkovic Kamelija (Aug.-Oct. 2003) "4-Hydroxynonenal and Neurodegenerative Diseases", Molecular Aspects of Medicine, 24(4-5): 293-303.
Zorova et al.(Jul. 1, 2018) "Mitochondrial Membrane Potential", Anal Biochem, 552: 50-59 (23 Pages).
Puente-Maestu et al. (Nov. 20, 2010) "Effects of exercise on mitochondrial DNA content in skeletal muscle of patients with COPD", Thorax, 66(2):121-127.
Knez el al. (Jun. 2015) "Correlates of Peripheral Blood Mitochondrial DNA copy number in a general population", Journal of Hypertension, 33(1): e2.
U.S. Appl. No. 17/169,271, "Methods of Treating Amyotrophic Lateral Sclerosis", filed Feb. 5, 2021, 37 pages.
Brenna et al. (Nov. 2020) "Plasma and Red Blood Cell Membrane Accretion and Pharmacokinetics of RT001 2 bis-Allylic 11, 11-02-Linoleic Acid Ethyl Ester) during Long Term Dosing in Patients", Journal of Pharmaceutical Sciences, 109(11):3496-3503.
Jun. 21, 2022 (WO) International Search Report & Written Opinion PCT/US22/15368.
Cho et al. "Role of Edaravone as a Treatment Option for Patients with Amyotrophic Lateral Sclerosis," Pharmaceuticals 2021, 1-14, 29 published Dec. 31, 2020. (Year: 2020).
McGeer et al. "Pharmacologic Approaches to the Treatment of Amyotrophic Lateral Sclerosis," Biodrugs 2005; 19 (1 ):31-37 (Year: 2005).
Mitsumoto et al. "Drug combination treatment in patients with ALS: Current status and future directions," Neurology 1996;47(Suppl 2); S1034107. (Year: 1996).
May 17, 2023 (WO) International Search Report & Written Opinion PCT/US2023/013051.
Berkers et al. "Topically Applied Ceramides Interact with the Stratum Corneum Lipid Matrix in Compromised Ex Vivo Skin" Pharm Res (2018) 35:48.
Office Action for U.S. Appl. No. 14/113,546 mailed on Sep. 16, 2014.
The Aldrich Catalog Handbook of Fine Chemicals 2003-2004, p. 140, catalog No. 48, 998-0 (2003-2004).
International Search Report and Written Opinion dated Nov. 29, 2012 for PCT/US2012/034833.
International Search Report and Written Opinion dated Nov. 29, 2012 for PCT/US2012/034835.
International Search Report and Written Opinion dated Nov. 29, 2012 for PCT/US2012/034836.
International Search Report dated Jun. 12, 2007 for PCT/GB2007/050112.
Jacquot et al.: Isotope Sensitive Branching and Kinetic Isotope Effects in the Reaction of Deuterated Arachidonic Acids with Human 12- and 15-Lipoxygenases. Biochemistry 47(27):7295-7303 (2008).
Japanese Journal of Clinical Medicine (Separate Volume) Syndrome classified as New Fields Series 13 Liver/Biliary Tract-based Syndrome (second edition) I Liver edition (the first volume) Sep. 20, 2010 p. 196 to 201 (2010).
Johnson et al, Potential role of dietary n-3 fatty acids in the prevention of dementia and macular degeneration. The American Journal of Clinical Nutrition 83(6):S1494-1498S (2006).
Journal of Biliary Tract & Pancreas 26(4):351-357 (2005).
Kelland et al; Stereochemistry of Lysine Formation by meso-Diaminopimelate Decarboxylase from Wheat Germ: Use of 1H-13C NMR Shift Correlation to Detect Stereospecific Deuterium Labeling. Biochemistry 24(13):3263-2367 (1985).
Kelly et al; Assessing the authenticity of single seed vegetable oils using fatty acid stable carbon isotope ratios (13C/12C). Food Chemistry 59(2):181-186 (1997).
King et al.: Mitochondria-derived reactive oxygen species mediate blue light-induced death of retinal pigment epithelial cells. Photochem Photobiol. 79(5):470-475 (2004).
Kishore et al; Partial 13C Isotopic Enrichment of Nucleoside Monophosphates: Useful Reporters for NMR Structural Studies. Nucleic Acids Research 33(18):e164 (2005).
Knapp et al; Temperature-dependent isotope effects in soybean lipoxygenase-I : Correlating hydrogen tunneling with protein dynamics. JACS Articles; J. Am. Chem. Soc. 124:3865-3874 (2002).
Kushner et al; Pharmacological uses and perspectives of heavy water and deuterated compounds. Canadian Journal of Physiology and Pharmacology 77:79-88 (1999).
Lambert D. Rationale and applications of lipids as prodrug carriers. European Journal of Pharmaceutical Sciences. 11(Suppl.2):S15-S27 (2000).
Lefkowitz et al; Where Does the Developing Brain Obtain its Docosahexaenoic Acid? Relative Contributions of Dietary a-Linolenic Acid, Docosahexaenoic Acid, and Body Stores in the Developing Rat. Pediatric Research 57(1):157-165 (2005).
Lei et al.: Dietary omega-3 Polyunsaturated Fatty Acids Enhance Adiponectin Expression and Protect Against Pressure Overload-Induced Left Ventricular Hypertrophy and Dysfunction. Journal of Cardial Failure, Churchill Livingstone, Naperville, IL, US 13(6):S79 (2007).
Levenson et al; The Healing of Rat Skin Wounds. Annals of Surgery 161(2):293-308 (1965).
Lichtenstein et al; Comparison of deuterated leucine, valine and lysine in the measurement of human apolipoprotein A-I and B-100 kinetics. Journal of Lipid Research 31(9):1693-1702 (1990).
Lin et al; Whole body distribution of deuterated linoleic and a-linolenic acids and their metabolites in the rat. Journal of Lipid Research 48:2709-2724 (2007).
Liuzzi et al.: Inhibitory effect of polyunsaturated fatty acids on MMP-9 release from microglial cells—implications for complementary multiple sclerosis treatment. Neurochem. Res. 32:2184-2193 (2007).
Mantena et al.: Mitochondrial dysfunction and oxidative stress in the pathogenesis of alcohol- and obesity-induced fatty liver diseases. Free Radical Biology & Medicine 44(7):1259-1272 (2008).
Mazza et al, Omega-3 fatty acids and antioxidants in neurological and psychiatric diseases: An overview. Progress in Neuro-Psychopharmacology & Biological Psychiatry, Oxford 31(1):12-26 (2007).
Mitsumoto et al.: Oxidative stress biomarkers in sporadic ALS Amyotroph Lateral Scler. 9(3):177-183 (2008).
Nass et al; Caenorhabditis elegans in Parkinson's Disease Drug Discovery: Addressing an Unmet Medical Need; Molecular Interventions 8(6):284-293 (2008).
Nelson et al.: Reduction of beta-Amyloid Levels by Novel Protein Kinase C epsilon Activators. Journal of Biological Chemistry 284(50):34514-34521 (2009).
Tamiya et al. Infra-red absorption spectra of deuterated aspartic acids. Spectrochimica Acta 18(7):895-905 (1962).
Notice of Reasons for Rejection dated Aug. 24, 2011 for Japanese Patent Application No. 2008-557833.
Oba et al; A simple rout to L-[5,5,6,6-D4] lysine starting from L-pyroglutamic acid. Japanese Journal of Deuterium Science 12(1):1-5 (2006).
Office Action for Japanese Patent Application No. 2014-508486 mailed on Dec. 25, 2015.
Office Action for Japanese Patent Application No. 2014-508487 mailed on Dec. 3, 2015.
Office Action for Japanese Patent Application No. 2014-508488 mailed on Dec. 4, 2015.
Office Action for Japanese Patent Application No. 2014-508489 mailed on Dec. 25, 2015.
Office Action for U.S. Appl. No. 14/551,450 mailed on Apr. 15, 2015 by U.S. Patent and Trademark Office.
Ovide-Bordeaux et al.: Docosahexaenoic acid affects insulin deficiency- and insulin resistance-induced alterations in cardiac mitochondria. Am J Physiol Regul Interg Comp Physiol 286:R519-R527 (2004).
Pedersen et al.: Protein modification by the lipid peroxidation product 4-hydroxynonenal in the spinal cords of amyotrophic lateral sclerosis patients. Annals of Neurology 44(5):819-824 (1998).

(56) References Cited

OTHER PUBLICATIONS

Peng et al.: Structural characterization of a pentadienyl radical intermediate formed during catalysis by prostaglandin H synthase-2. J Am Chem Soc. 123(15):3609-3610 (2001).
Raap et al; Enantioseletive syntheses of isotopically labeled a-amino acids. Preparation of (c-13C)-L-a-aminoadipic acid and five isotopomers of L-lysine with 13C, 15N, and 2H in the b-and c-positions. Recueil de Travaux Chimiques de Pays-Bas 109(4):277-286 (1990).
Rapoport et al; Delivery and turnover of plasma-derived essential PUFAs in mammalian brain. Journal of Lipid Research 42:678-685 (2001).
Reddy P. H., Mitochondrial medicine for aging and neurodegenerative diseases. Neuromolecular Med. 10(4):291-315 (2008).
Ren et al; Simultaneous metabolic labeling of cells with multiple amino acids: localization and dynamics of histone acetylation and methylation. Proteomics: Clinical Applications 1(1):130-142 (2007).
Riediger et al.: A Systemic Review of the Roles of n-3 Fatty Acids in Health and Disease. Journal of the American Dietetic Association 109(4):668-679 (2009).
Rohwedder et al; Measurement of the Metabolic Interconversion of Deuterium-Labeled Fatty Acids by Gas Chromatography/Mass Spectrometry. Lipids 25(7):401-405 (1990).
Rosen et al; Effect of Deuterium Oxide on Wound Healing, Collagen and Metabolism of Rats. New England Journal of Medicine 270(22):1142-1149 (1964).
Rustin et al.: Effect of idebenone on cardiomyopathy in Friedreich's ataxia: a preliminary study. Lancet 354 (9177):477-479 (1999).
Salem et al; Arachidonic and docosahexaenoic acids are biosynthesized from their 18-carbon precursors in human infants. Proc. Natl. Acad. Sci. 93:49-54 (1996).
Scholl et al; Synthesis of 5,5,6,6-D4-L-lystine-aflatoxin B1 for use as a mass spectrometric internal standard. Journal of Labelled Compounds & Radiopharmaceuticals 47(11):807-815 (2004).
Schutt et al.: Proteins modified by malondialdehyde, 4-hydroxynonenal, or advanced glycation end products in lipofuscin of human retinal pigment epithelium. Invest Ophthalmol Vis Sci. 44(8):3663-3668 (2003).
Separate Volume/Advances in Medical Science Oxidative Stress Ver.2 Oct. 5, 2006:23-27 (2006).
Serhiyenko V et al.: Simvastatin and Omega-Polyunsaturated Fatty Acids in the Treatment of Cardiomyopathy in Type 2 Diabetes Mellitus Patients. Atherosclerosis Supplements, Elsevier, Amsterdam, NL 9(1):203 (2008).

* cited by examiner

METHODS OF TREATING AMYOTROPHIC LATERAL SCLEROSIS

CROSS-REFERENCE TO RELATED APPLICATION(S)

This application is a continuation of U.S. patent application Ser. No. 17/391,909, filed Aug. 2, 2021, which is a continuation-in-part of Ser. No. 17/169,271, filed Feb. 5, 2021, now. U.S. Pat. No. 11,351,143, issued Jun. 7, 2022, which is incorporated herein by reference in its entirety.

TECHNICAL FIELD

Disclosed are methods for inhibiting the progression of neurodegenerative diseases in humans. The methods use a specific dosing regimen to treat a patient suffering from a neurodegenerative disease treatable with a deuterated arachidonic acid or a prodrug thereof. In particular, the dosing regimen provides for rapid onset to a therapeutic concentration in vivo of deuterated arachidonic acid at a level where the progression of the disease is markedly reduced.

BACKGROUND

There are a number of debilitating neurodegenerative diseases in humans which despite the best efforts of researchers remain incurable and often fatal. As such, the attending clinician attempts to slow the progression of the disease and, where possible, maintain the quality of life for the patient for as long as possible. Examples of such neurodegenerative diseases include the following:

- amyotrophic lateral sclerosis (ALS) which is a late-onset, progressive neurological disease with its corresponding pathological hallmarks including progressive muscle weakness, muscle atrophy and spasticity all of which reflect the degeneration and death of upper or lower motor neurons. Once diagnosed, most patients undergo a rapid rate of disease progression terminating in death typically within 3 to 4 years with some patients succumbing even earlier;
- tauopathy is a subgroup of Lewy body diseases or proteinopathies and comprises neurodegenerative conditions involving the aggregation of tau protein into insoluble tangles.

These aggregates/tangles form from hyperphosphorylation of tau protein in the human brain. Specific conditions related to tauopathy include, but are not limited to, argyrophilic grain disease (AGD), chronic traumatic encephalopathy (CTE), corticobasal degeneration (CBD), frontotemporal dementia and parkinsonism linked to chromosome 17 (FTDP-17), ganglioglioma, gangliocytoma, lipofuscinosis, lytico-bodig disease, meningioangiomatosis, pantothenate kinase-associated neurodegeneration (PKAN), Pick's disease, postencephalitic parkinsonism, primary age-related tauopathy (PART), Steele-Richardson-Olszewski syndrome (SROS), and subacute sclerosing panencephalitis (SSPE). Wang et al., Nature Rev. Neurosci. 2016; 17:5 and Arendt et al., Brain Res. Bulletin 2016; 126:238. Tauopathies often overlap with synucleinopathies.

Steele-Richardson-Olszewski syndrome or progressive supranuclear palsy (PSP) is one example of a neurodegenerative disease mediated at least in part by tauopathy and involves the gradual deterioration and death of specific volumes of the brain. The condition leads to symptoms including loss of balance, slowing of movement, difficulty moving the eyes, and dementia. A variant in the gene for tau protein called the HI haplotype, located on chromosome 17, has been linked to PSP. Besides tauopathy, mitochondrial dysfunction seems to be a factor involved in PSP. Especially, mitochondrial complex I inhibitors are implicated in PSP-like brain mJunes;

- Friedreich's ataxia is an autosomal-recessive genetic disease that causes difficulty walking, a loss of sensation in the arms and legs, and impaired speech that worsens over time. The pathology of this neurodegenerative disease involves degeneration of nerve tissue in the spinal cord;
- Huntington's disease is a fatal genetic disorder that causes the progressive breakdown of nerve cells in the brain;
- Corticobasal disorder (CBD) is a rare neurodegenerative disease characterized by gradual worsening problems with movement, speech, memory and swallowing. It's often also called corticobasal syndrom (CBS). CBD is caused by increasing numbers of brain cells becoming damaged or dying over time;
- Frontotemporal dementia (FTD) is a neurodegenerative disease and a common cause of dementia. It is characterized by a group of disorders that occur when nerve cells in the frontal temporal lobes of the brain are lost thereby causing the lobes to shrink. FTD can affect behavior, personality, language, and movement;
- Nonfluent variant primary progressive aphasia (nfvPPA) occurs as a result of a build up of one of two proteins, either tau or TPD-43, usually in the front left part of the brain. That part of the brain controls speech and language. As more of the protein builds up in those brain cells, the cells lose their ability to function and eventually die. As more cells die, the affected portion of the brain shrinks; and
- late onset Tay-Sachs is a very rare genetic neurodegenerative disease in which fatty compounds, called gangliosides, do not break down fully because the body produces too little of the enzyme hexosaminidase A (or hex A). Over time, gangliosides build up in the brain and damage brain nerve cells. This affects a person's mental functioning.

There remains a need for treatments for these and other neurodegenerative diseases.

SUMMARY

In one embodiment, methods are disclosed that significantly attenuate the progression of neurodegenerative diseases treatable by administration of 11,11-D2-linoleic acid or an ester thereof. The 11,11-D2-linoleic acid or ester thereof is hepatically converted to 13,13-arachidonic acid—the active moiety. Such administration is delivered with a dosing regimen that comprises both a loading regimen and a maintenance regimen. The loading regimen ensures that there is a rapid onset to therapeutic levels of the 13,13-D2-arachidonic acid in vivo to attenuate disease progression thereby retaining more functionality in the patient as compared to dosing regimens that require longer periods of time to achieve therapeutic levels. The maintenance dose ensures that the therapeutic levels of 13,13-D2-arachidonic acid are maintained in the patient during therapy.

In one embodiment, 11,11-D2-linoleic acid or an ester thereof is administered such that upon ingestion and absorption, in vivo deesterification of the ester is followed by hepatic conversion of a portion of the deuterated linoleic acid so as to generate 13,13-D2-arachidonic acid. For example, the deuterated linoleic acid or an ester thereof constitute both an essential fatty acid but also a prodrug of 13,13-D2-arachidonic acid.

Without being limited by theory, once generated, 13,13-D2-arachidonic acid is systemically absorbed into cells such as the cell membrane and the mitochondria. In neurons, this deuterated arachidonic acid stabilizes the deuterated arachidonic acid against oxidative damage. This, in turn, stops the cascade of lipid peroxidation, thereby minimizing damage to the motor neurons. When concentrations of this deuterated arachidonic acid reach a therapeutic level in the motor neurons, the disease progression of neurodegenerative diseases is significantly attenuated.

The methods described herein provide for rapid onset of a therapeutic concentration of 13,13-D2-arachidonic acid in vivo so as to minimize unnecessary loss of functionality in the treated patients suffering from a neurodegenerative disease. In one embodiment, there is provided a method for reducing disease progression of a neurodegenerative disease in an adult patient treatable with 13,13-D2-arachidonic acid while providing for rapid onset of therapy, the method comprising administering 11,11-D2-linoleic acid or an ester thereof to the patient with a dosing regimen that comprises a primer dose and a maintenance dose. In an embodiment, the primer dose comprises periodic administration of 11,11-D2-linoleic acid or an ester thereof. In an embodiment, the primer dose comprises about 7 grams to about 12 grams of 11,11-D2-linoleic acid or an ester thereof per day. In an embodiment, the primer dose is continued for about 30 days to about 45 days, e.g., to rapidly achieve a therapeutic concentration of 13,13-D2-arachidonic acid in vivo due to hepatic conversion of a portion of said 11,11-D2-arachidonic acid to 13,13-D2-arachidonic acid, thereby reducing the rate of disease progression. In an embodiment, after completion of the primer dose, the maintenance dose is periodically administered. In an embodiment, no more than about 65% of the loading dose of 11,11-D2-linoleic acid or an ester thereof per day is administered. In an embodiment, the therapeutic concentration of 13,13-D2-arachidonic acid is maintained in vivo such that a reduced rate of disease progression is maintained.

In an embodiment, the reduced rate of disease progression is evaluated when compared to the rate of disease progression measured prior to initiation of said method. In an embodiment, each of said neurodegenerative diseases is mediated at least in part by lipid peroxidation of polyunsaturated fatty acids in neurons of the patient suffering from said neurodegenerative disease.

In one embodiment, said neurodegenerative disease is amyotrophic lateral sclerosis, Huntington's Disease, progressive supernuclear palsy (PSP), Friedreich's ataxia, APO-e4 Alzheimer's Disease, corticobasal disorder (CBD), frontotemporal dementia (FTD), nonfluent variant primary progressive aphasia (nfvPPA), other tauopathies, or late onset Tay-Sachs.

In one embodiment, said periodic administration of the loading dose comprises administration of about 9 grams of 11,11-D2-linoleic acid or an ester thereof (e.g., about 8.6 g) per day for at least 5 days per week and preferably 7 days a week.

In one embodiment, the periodic administration of the maintenance dose of 11,11-D2-linoleic acid or an ester thereof per day comprises no more than 55% of the loading dose which is administered at least once a month. In another embodiment, the maintenance dose comprises no more than 35% of the loading dose which is administered at least once a month.

In one embodiment, the periodic administration of the maintenance dose is calibrated to be an amount of 11,11-D2-linoleic acid or an ester thereof sufficient to replace the amount of 13,13-D2-arachidonic acid removed from the body taking into account the hepatic conversion of a portion of 11,11-D2-linoleic acid to 13,13-D2-arachidonic acid.

In one embodiment, the percent reduction in the rate of disease progression is determined by:

measuring a natural rate of disease progression in a patient or an average natural rate of disease progression in a cohort of patients prior to initiation of therapy per the methods described herein;

measuring the rate of disease progression in said patient or cohort of patients during a period of compliance with the periodic administration of both the loading step and the maintenance step; and after a set period of time from the start of therapy, calculating the difference between the natural rate and the rate during the period of compliance, dividing the difference by the rate of disease progression during the natural history of the patient, and multiplying by 100.

In one embodiment, the set period of time is between about 1 month and about 24 months, for example about 3 months, about 6 months or about 12 months, or about 18 months or about 24 months.

In one embodiment, the methods described herein further comprise restricting the patient's consumption of excessive dietary polyunsaturated fatty acids during administration of said primer and said maintenance doses.

In one embodiment, there is provided a kit of parts comprising a set of capsules each comprising a partial loading dose of 11,11-D2-linoleic acid or an ester thereof such that two or more of said capsules comprise a complete loading dose per day.

In one embodiment, there is provided a kit of parts comprising a set of capsules each comprising a partial loading dose of 11,11-D2-linoleic acid or an ester thereof such that nine of said capsules comprise a complete loading dose per day.

In one embodiment, there is provided a kit of parts comprising a set of capsules each comprising a partial maintenance dose of 11,11-D2-linoleic acid or an ester thereof such that two or more of said capsules comprise a complete maintenance dose per day.

In one embodiment, there is provided a kit of parts comprising a set of capsules each comprising a partial maintenance dose of 11,11-D2-linoleic acid or an ester thereof such that five of said capsules comprise a complete maintenance dose per day.

In one embodiment, the percent change between the rate of disease progression occurring during the natural history of the patient and the decrease in the rate of disease progression during therapy is at least 25%, at least 30%, preferably at least 40%, more preferably at least 65% and most preferably greater than 70% or 80% after 1 or 3 months. Accordingly, in some embodiments, methods disclosed herein provide for determining a percent reduction in the rate of disease progression by (i) determining a natural rate of disease progression in a patient or an average natural rate of disease progression in a cohort of patients, (ii) determining the rate of disease progression in the patient or cohort of patients during a period of compliance with administration of deuterated arachidonic acid, an ester thereof, or a prodrug thereof, and (iii) measuring the difference between the natural rate of disease progression and the rate during the period of compliance, and dividing the difference by the natural rate of disease progression. The numerical value is then normalized by multiplying by 100.

In one embodiment, the deuterated linoleic acid ester isl 1,11-D2-linoleic acid ethyl ester.

In one embodiment, whether a therapeutic concentration of 13,13-D2-arachidonic acid has been reached in neurons is measured using a reporter cell. In an embodiment, the reporter cells are red blood cells. In the case of red blood cells, a concentration of 13,13-D2-arachidonic acid of at least about 3% based on the total number of arachidonic acid, including deuterated arachidonic acid, contained in the red blood cells has been found to correlate with therapeutic results. Alternatively, the therapeutic concentration of 13,13-D2-arachidonic acid in the neurons can be extrapolated from the concentration of 11,11-D2-linoleic acid in a reporter cell, such as red blood cells, as per the Examples below. See, e.g., U.S. Provisional Patent Application No. 63/177,794, filed Apr. 21, 2021, which is incorporated by reference in its entirety.

In one embodiment, the patients are placed on a diet that restricts intake of excessive amounts of linoleic acid, arachidonic acid, and/or other PUFA compounds so as to avoid insufficient uptake of the deuterated linoleic acid by the body. Generally, dietary components that contribute to excessive amounts of PUFA consumed are restricted. Such dietary components include, for example, fish oil pills, products that contain high levels of PUFAs, such as salmon; patients on conventional feeding tubes may also have excessive PUFA intake. In a preferred embodiment, the methods described herein include both the dosing regimen described above as well as placing the patients on a restrictive diet that avoids excessive ingestion of PUFA components.

In one embodiment is provided a method for reducing the rate of disease progression in a patient suffering from a neurodegenerative disease treatable with 11,11-D2-linoleic acid, which method comprises administering 11,11-D2-linoleic acid or an ester thereof to the patient with a dosing regimen that comprises a primer dosing and a maintenance dosing schedule which comprise:

a) said first dosing component comprises administering to said patient primer dose of 11,11-D2-linoleic acid or an ester thereof in an amount to sufficient and for a period of time to allow for reduction in the rate of disease progression within no more than about 45 days from start of dosing;

b) subsequently following said primer dose, initiating a maintenance dosing to said patient said dosing comprises an amount of 11,11-D2-linoleic acid or an ester thereof in an amount sufficient to maintain the concentration of 13,13-D2-arachidonic acid in the motor neurons wherein the amount of 11,11-D2-linoleic acid or ester thereof administered in said maintenance dose is less than the amount administered in said primer dose; and optionally:

c) monitoring the concentration of 13,13-D2-arachidonic acid in the patient to ensure that the patient is maintaining a therapeutic concentration of 13,13-D2-arachidonic acid; and d) increasing the dosing of 11,11-D2-linoleic acid or an ester thereof when said concentration of 13,13-D2-arachidonic acid is deemed to be less than a therapeutic amount.

DETAILED DESCRIPTION

Figure 1:
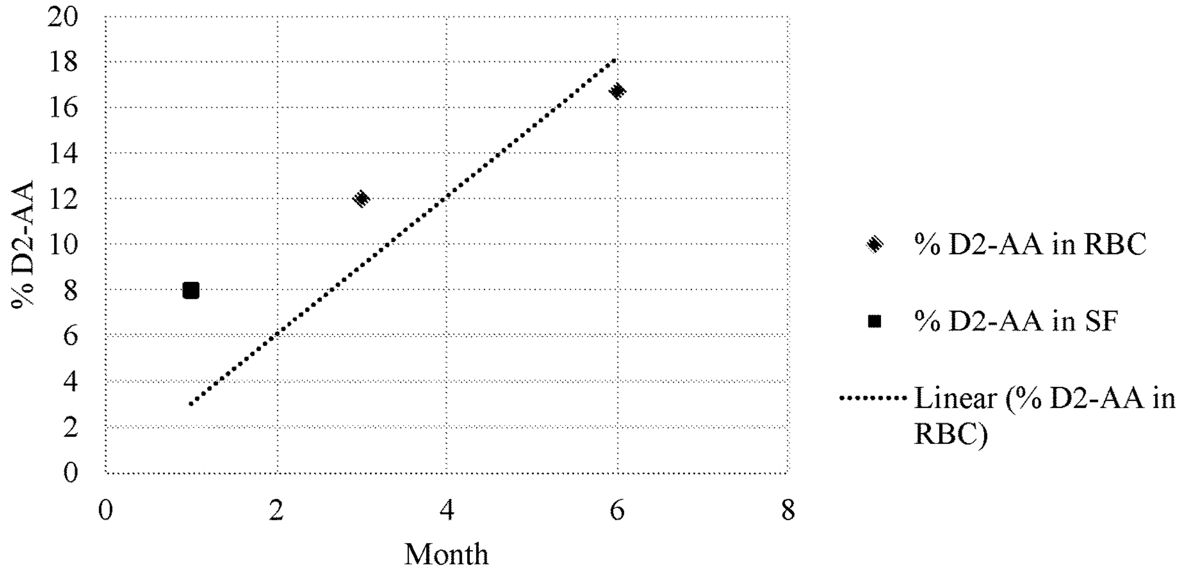
FIG. 1 is a graph showing the percent of 13,13-D2-Arachidonic Acid in red blood cells (RBC) and spinal fluid (SF) at the indicated time points after start of treatment with 11,11-D2-Linoleic Acid in an adult patient.

In one embodiment, methods are disclosed that significantly attenuate the progression of neurodegenerative diseases treatable by administration of 11,11-D2-linoleic acid or an ester thereof. The 11,11-D2-linoleic acid or ester thereof is hepatically converted to 13,13-arachidonic acid—the active moiety. Such administration is delivered with a dosing regimen that comprises both a loading regimen and a maintenance regimen. The loading regimen ensures that there is a rapid onset to therapeutic levels of the 13,13-D2-arachidonic acid in vivo to attenuate disease progression thereby retaining more functionality in the patient as compared to dosing regimens that require longer periods of time to achieve therapeutic levels. The maintenance dose ensures that the therapeutic levels of 13,13-D2-arachidonic acid are maintained in the patient during therapy.

In one embodiment, 11,11-D2-linoleic acid or an ester thereof is administered such that upon ingestion and absorption, in vivo deesterification of the ester is followed by hepatic conversion of a portion of the deuterated linoleic acid so as to generate 13,13-D2-arachidonic acid. For example, the deuterated linoleic acid or an ester thereof constitute both an essential fatty acid but also a prodrug of 13,13-D2-arachidonic acid.

Without being limited by theory, once generated, 13,13-D2-arachidonic acid is systemically absorbed into cells such as the cell membrane and the mitochondria. In neurons, this deuterated arachidonic acid stabilizes the deuterated arachidonic acid against oxidative damage. This, in turn, stops the cascade of lipid peroxidation, thereby minimizing damage to the motor neurons. When concentrations of this deuterated arachidonic acid reach a therapeutic level in the motor neurons, the disease progression of neurodegenerative diseases is significantly attenuated.

The methods described herein provide for rapid onset of a therapeutic concentration of 13,13-D2-arachidonic acid in vivo so as to minimize unnecessary loss of functionality in the treated patients suffering from a neurodegenerative disease. In one embodiment, there is provided a method for reducing disease progression of a neurodegenerative disease in an adult patient treatable with 13,13-D2-arachidonic acid while providing for rapid onset of therapy, the method comprising administering 11,11-D2-linoleic acid or an ester thereof to the patient with a dosing regimen that comprises a primer dose and a maintenance dose. In an embodiment, the primer dose comprises periodic administration of 11,11-D2-linoleic acid or an ester thereof. In an embodiment, the primer dose comprises about 7 grams to about 12 grams of 11,11-D2-linoleic acid or an ester thereof per day. In an embodiment, the primer dose is continued for about 30 days to about 45 days, e.g., to rapidly achieve a therapeutic concentration of 13,13-D2-arachidonic acid in vivo due to hepatic conversion of a portion of said 11,11-D2-arachidonic acid to 13,13-D2-arachidonic acid, thereby reducing the rate of disease progression. In an embodiment, after completion of the primer dose, the maintenance dose is periodically administered. In an embodiment, no more than about 65% of the loading dose of 11,11-D2-linoleic acid or an ester thereof per day is administered. In an embodiment, the therapeutic concentration of 13,13-D2-arachidonic acid is maintained in vivo such that a reduced rate of disease progression is maintained.

In an embodiment, the reduced rate of disease progression is evaluated when compared to the rate of disease progression measured prior to initiation of said method. In an embodiment, each of said neurodegenerative diseases is mediated at least in part by lipid peroxidation of polyunsaturated fatty acids in neurons of the patient suffering from said neurodegenerative disease.

In one embodiment, said neurodegenerative disease is amyotrophic lateral sclerosis, Huntington's Disease, progressive supernuclear palsy (PSP), Friedreich's ataxia, APO-e4 Alzheimer's Disease, corticobasal disorder (CBD), frontotemporal dementia (FTD), nonfluent variant primary progressive aphasia (nfvPPA), other tauopathies, or late onset Tay-Sachs.

In one embodiment, said periodic administration of the loading dose comprises administration of about 9 grams of 11,11-D2-linoleic acid or an ester thereof (e.g., about 8.6 g) per day for at least 5 days per week and preferably 7 days a week.

In one embodiment, the periodic administration of the maintenance dose of 11,11-D2-linoleic acid or an ester thereof per day comprises no more than 55% of the loading dose which is administered at least once a month. In another embodiment, the maintenance dose comprises no more than 35% of the loading dose which is administered at least once a month.

In one embodiment, the periodic administration of the maintenance dose is calibrated to be an amount of 11,11-D2-linoleic acid or an ester thereof sufficient to replace the amount of 13,13-D2-arachidonic acid removed from the body taking into account the hepatic conversion of a portion of 11,11-D2-linoleic acid to 13,13-D2-arachidonic acid.

In one embodiment, the percent reduction in the rate of disease progression is determined by:

- measuring a natural rate of disease progression in a patient or an average natural rate of disease progression in a cohort of patients prior to initiation of therapy per the methods described herein;
- measuring the rate of disease progression in said patient or cohort of patients during a period of compliance with the periodic administration of both the loading step and the maintenance step; and
- after a set period of time from the start of therapy, calculating the difference between the natural rate and the rate during the period of compliance, dividing the difference by the rate of disease progression during the natural history of the patient, and multiplying by 100.

In one embodiment, the set period of time is between about 1 month and about 24 months, for example about 3 months, about 6 months or about 12 months, or about 18 months or about 24 months.

In one embodiment, the methods described herein further comprise restricting the patient's consumption of excessive dietary polyunsaturated fatty acids during administration of said primer and said maintenance doses.

In one embodiment, there is provided a kit of parts comprising a set of capsules each comprising a partial loading dose of 11,11-D2-linoleic acid or an ester thereof such that two or more of said capsules comprise a complete loading dose per day.

In one embodiment, there is provided a kit of parts comprising a set of capsules each comprising a partial loading dose of 11,11-D2-linoleic acid or an ester thereof such that nine of said capsules comprise a complete loading dose per day.

In one embodiment, there is provided a kit of parts comprising a set of capsules each comprising a partial maintenance dose of 11,11-D2-linoleic acid or an ester thereof such that two or more of said capsules comprise a complete maintenance dose per day.

In one embodiment, there is provided a kit of parts comprising a set of capsules each comprising a partial maintenance dose of 11,11-D2-linoleic acid or an ester thereof such that five of said capsules comprise a complete maintenance dose per day.

In one embodiment, the percent change between the rate of disease progression occurring during the natural history of the patient and the decrease in the rate of disease progression during therapy is at least 25%, at least 30%, preferably at least 40%, more preferably at least 65% and most preferably greater than 70% or 80% after 1 or 3 months. Accordingly, in some embodiments, methods disclosed herein provide for determining a percent reduction in the rate of disease progression by (i) determining a natural rate of disease progression in a patient or an average natural rate of disease progression in a cohort of patients, (ii) determining the rate of disease progression in the patient or cohort of patients during a period of compliance with administration of deuterated arachidonic acid, an ester thereof, or a prodrug thereof, and (iii) measuring the difference between the natural rate of disease progression and the rate during the period of compliance, and dividing the difference by the natural rate of disease progression. The numerical value is then normalized by multiplying by 100.

In one embodiment, the deuterated linoleic acid ester isl 1,11-D2-linoleic acid ethyl ester.

In one embodiment, whether a therapeutic concentration of 13,13-D2-arachidonic acid has been reached in neurons is measured using a reporter cell. In an embodiment, the reporter cells are red blood cells. In the case of red blood cells, a concentration of 13,13-D2-arachidonic acid of at least about 3% based on the total number of arachidonic acid, including deuterated arachidonic acid, contained in the red blood cells has been found to correlate with therapeutic results. Alternatively, the therapeutic concentration of 13,13-D2-arachidonic acid in the neurons can be extrapolated from the concentration of 11,11-D2-linoleic acid in a reporter cell, such as red blood cells, as per the Examples below. See, e.g., U.S. Provisional Patent Application No. 63/177,794, filed Apr. 21, 2021, which is incorporated by reference in its entirety.

In one embodiment, the patients are placed on a diet that restricts intake of excessive amounts of linoleic acid, arachidonic acid, and/or other PUFA compounds so as to avoid insufficient uptake of the deuterated linoleic acid by the body. Generally, dietary components that contribute to excessive amounts of PUFA consumed are restricted. Such dietary components include, for example, fish oil pills, products that contain high levels of PUFAs, such as salmon; patients on conventional feeding tubes may also have excessive PUFA intake. In a preferred embodiment, the methods described herein include both the dosing regimen described above as well as placing the patients on a restrictive diet that avoids excessive ingestion of PUFA components.

In one embodiment is provided a method for reducing the rate of disease progression in a patient suffering from a neurodegenerative disease treatable with 11,11-D2-linoleic acid, which method comprises administering 11,11-D2-linoleic acid or an ester thereof to the patient with a dosing regimen that comprises a primer dosing and a maintenance dosing schedule which comprise:

a) said first dosing component comprises administering to said patient primer dose of 11,11-D2-linoleic acid or an ester thereof in an amount to sufficient and for a period of time to allow for reduction in the rate of disease progression within no more than about 45 days from start of dosing;

b) subsequently following said primer dose, initiating a maintenance dosing to said patient said dosing comprises an amount of 11,11-D2-linoleic acid or an ester thereof in an amount sufficient to maintain the concentration of 13,13-D2-arachidonic acid in the motor neurons wherein the amount of 11,11-D2-linoleic acid or ester thereof administered in said maintenance dose is less than the amount administered in said primer dose; and optionally:

c) monitoring the concentration of 13,13-D2-arachidonic acid in the patient to ensure that the patient is maintaining a therapeutic concentration of 13,13-D2-arachidonic acid; and d) increasing the dosing of 11,11-D2-linoleic acid or an ester thereof when said concentration of 13,13-D2-arachidonic acid is deemed to be less than a therapeutic amount.

This invention is directed to methods for treating neurodegenerative diseases to significantly slow the rate of disease progression in a patient. In one embodiment, the methods of this invention include a dosing regimen that is sufficient to provide a therapeutic level of deuterated arachidonic acid in the motor neurons. In another embodiment, the methods described herein comprise a daily or periodic primer dose that accelerates delivery of deuterated arachidonic acid to the diseased neurons of the patient. This primer dose is continued for a sufficient period of time to achieve a therapeutic concentration of a deuterated arachidonic acid in vivo. At that point, a daily or periodic maintenance dose is employed to maintain the therapeutic concentration of the deuterated arachidonic acid.

Prior to discussing this invention in more detail, the following terms will first be defined. Terms that are not defined are given their definition in context or are given their medically acceptable definition.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the term "optional" or "optionally" means that the subsequently described event or circumstance can or cannot occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 15, % 10%, 5%, 1%, or any subrange or subvalue there between. Preferably, the term "about" when used with regard to a dose amount means that the dose may vary by +/−10%.

As used herein, the term "comprising" or "comprises" is intended to mean that the compositions and methods include the recited elements, but not excluding others.

As used herein, the term "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the term "consisting of" shall mean excluding more than trace elements of other ingredients and substantial method steps. Embodiments defined by each of these transition terms are within the scope of this invention.

As used herein, the term "linoleic acid" refers to the compound and a pharmaceutically acceptable salt thereof having the formula provided below and having the natural abundance of deuterium (i.e., about 0.0156% naturally-occurring deuterium) at each hydrogen atom:

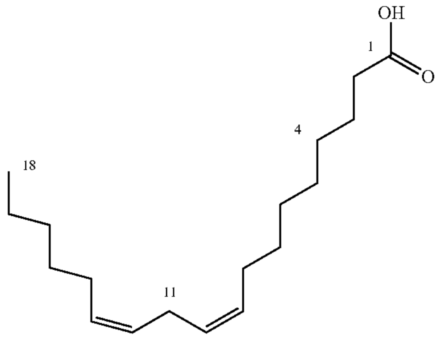 [SMILES: CCCCC/C=C\C/C=C\CCCCCCCC(=O)O]

Esters of linoleic acid are formed by replacing the —OH group with —OR Such esters are as defined herein below.

As used herein and unless the context dictates otherwise, the term "deuterated linoleic acid or an ester thereof" refers to linoleic acid or ester compounds comprising one or two deuterium atoms at the 11 position thereof and optionally additional deuterium atoms at other positions within the molecule including at position 8. Specific compounds encompassed by this definition include by way of example only 11-D1-linoleic acid, 11,11-D2-linoleic acid, 8,11-D2-linoleic acid, 8,11,11-D3-linoleic acid and 8,8,11,11-D4-linoleic acid as well as esters of any one of these compounds. Additional stabilization of the bis-allylic position could also include replacement of one or more of bis-allylic carbon atoms with a heavy isotope, alone or in conjunction with the deuteration (or tritiation), as the isotope effect (IE) resulting in stabilization of a bond with heavy isotopes is additive per long-established and fundamental chemical principles. (Westheimer, *Chem. Rev.* (1961), 61:265-273; Shchepinov, *Rejuvenation Res.*, (2007), 10:47-59; Hill et al., *Free Radie. Biol. Med,* (2012), 53:893-906; Andreyev et al., *Free Radie. Biol. Med,* (2015), 82:63-72. Bigeleisen, J. The validity of the use of tracers to follow chemical reactions. *Science,* (1949), 110:14-16.

As used herein, arachidonic acid has the numbering system as described below:

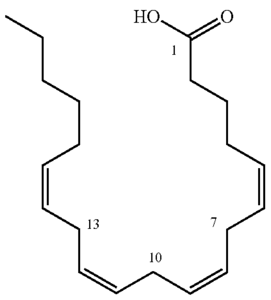 [SMILES: CCCCC/C=C\C/C=C\C/C=C\C/C=C\CCCC(=O)O]

where each of positions 7, 10 and 13 are bis-allylic positions within the structure.

As used herein and unless the context dictates otherwise, the term "deuterated arachidonic acid or an ester thereof" refers to 13,13-D2-arachidonic acid or a C1-C6 alkyl ester, glycerol ester (including monoglycerides, diglycerides and triglycerides), sucrose esters, phosphate esters, and the like. The particular ester group employed is not critical provided that the ester group is pharmaceutically acceptable (non-toxic and biocompatible).

As used herein and unless the context dictates otherwise, the term "an ester thereof" refers to a C1-C6 alkyl ester, glycerol ester (including monoglycerides, diglycerides and triglycerides), sucrose esters, phosphate esters, and the like. The particular ester group employed is not critical provided that the ester is pharmaceutically acceptable (non-toxic and biocompatible).

As used herein, the term "phospholipid" refers to any and all phospholipids that are components of the cell membrane. Included within this term are phosphatidylcholine, phosphatidylethanolamine, phosphatidylserine, and sphingomyelin. In the motor neurons, the cell membrane is enriched in phospholipids comprising arachidonic acid.

As used herein, the term "pathology of a disease" refers to the cause, development, structural/functional changes, and natural history associated with that disease. The term "natural history" means the progression of the disease in the absence of treatment per the methods described herein.

As used herein, the term "reduced rate of disease progression" means that the rate of disease progression is attenuated after initiation of treatment as compared to the patient's natural history. In one case, the rate of reduction in disease progression using the methods described herein results in a percentage reduction of at least 25% lower or at least 30% lower at a time point, e.g. 1 month to 24 months, e.g., 3 or 6 months, after initiation of therapy when compared to the natural history of the patient.

The term "therapeutic concentration" means a concentration of a deuterated arachidonic acid that reduces the rate of disease progression by at least 25% or at least 30%. Since obtaining the concentration of a deuterated arachidonic acid in the motor neurons or in the spinal fluid of a patient is either not feasible or optimal, the therapeutic concentration is based on the concentration of either deuterated linoleic acid or deuterated arachidonic acid found in red blood cells as provided in the Examples below. Accordingly, any reference made herein to a therapeutic concentration of deuterated arachidonic acid is made by evaluating its concentration in red blood cells.

Alternatively, the reduction in the rate of disease progression is confirmed by a reduction in the downward slope (flattening the curve) of a patient's relative muscle functionality during therapy as compared to the downward slope found in the patient's natural history.

Typically, the differential between the downward slope measured prior to treatment and the slope measured after at least 90 days from initiation of treatment has a flattening level of at least about 30%. So, a change of 7.5 degrees (e.g., a downward slope of 25 degrees during the natural history that is reduced to a downward slope of 17.5 degrees provides for a 40% decrease in the slope). In any case, the reduction in downward slope evidence that the patient has a reduced rate of disease progression due to the therapy.

As used herein, the term "patient" refers to a human patient or a cohort of human patients suffering from a neurodegenerative disease treatable by administration of 11,11-D2-linoleic acid or an ester thereof. The term "adult patient" refers to a subject over 18 years of age and suffering from a neurodegenerative disease treatable by administration of 11,11-D2-linoleic acid or an ester thereof. As used herein, the term "loading or primer amount" refers to an amount of a deuterated linoleic acid or an ester thereof or a deuterated arachidonic acid or an ester thereof that is sufficient to provide for a reduced rate of disease progression within at least about 45 days after initiation of administration and preferably within 30 days. The amount so employed is loaded such that the patient has a stabilized rate of disease progression within this time period. When less than a loading amount is used, it is understood that such can provide therapeutic results but will not achieve the same level of reduction in disease progression. Given the progressive nature of neurodegenerative diseases, those dosing regimens that achieve the best reduction in the rate of disease progression are preferred as they are associated with the patient having less loss of muscle functionality over a given period of time.

The methods described herein are based on the discovery that the primer doses of 11,11-D2-linoleic acid or an ester thereof employed to date are well tolerated by patients and provide for rapid onset of a sufficient amount of 13,13-D2-arachidonic acid to provide for a reduced and stabilized rate of disease progression.

As used herein, the term "maintenance dose" refers to a dose of 11,11-D2-linoleic acid or an ester thereof that is less than the primer dose and is sufficient to maintain a therapeutic concentration of deuterated arachidonic acid in the cell membrane of red blood cells and, hence, in the cell membrane of motor neurons, so as to retain a stable rate of disease progression.

As used herein, the term "periodic dosing" refers to a dosing schedule that substantially comports to the dosing described herein. Stated differently, periodic dosing includes a patient who is compliant at least 75 percent of the time over a 30-day period and preferably at least 80% compliant. In embodiments, the dosing schedule contains a designed pause in dosing. For example, a dosing schedule that provides dosing 6 days a week is one form of periodic dosing.

Another example is allowing the patient to pause administration for from about 3 or 7 or more days, e.g. due to personal reasons, provided that the patient is otherwise at least 75 percent compliant.

The term "cohort" refers to a group of at least 2 patients whose results are to be averaged.

As used herein, the term "pharmaceutically acceptable salts" of compounds disclosed herein are within the scope of the methods described herein and include acid or base addition salts which retain the desired pharmacological activity and is not biologically undesirable (e.g., the salt is not unduly toxic, allergenic, or irritating, and is bioavailable). When the compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound has an acidic group, such as for example, a carboxylic acid group, it can form salts with metals, such as alkali and earth alkali metals (e.g., Na+, Li+, K+, Ca2+, Mg2+, zn2+), ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

The phrase "excessive amounts of PUFAs," "excessive PUFA intake," and the like refer to intake of total PUFAs (e.g., total amount of PUFAs consumed per day) that result in reduced conversion of 11,11-D2-linoleic acid to 13,13-D2-arachidonic acid compared to a diet lower in total PUFA intake. In embodiments, the patient is on a diet that restricts intake of linoleic acid, arachidonic acid, and/or other PUFA compounds. The amount of PUFAs that can be consumed by a patient is variable, depending on numerous factors such as the patient's health, weight, age, other medications being taken, liver function, metabolism, and the like.

In general, a patient on a 2,000 calorie per day diet consumes up to about 22 grams of polyunsaturated fatty acids (news.christianacare.org/2013/04/nutrition-numbers-revealed-fat-intake/), of which about 14 grams are linoleic acid when averaged for men and women (www.ncbi.nlm-.nih.gov/pmc/articles/PMC3650500/). In addition, only about 10% of the average amount of linoleic acid consumed is hepatically converted to arachidonic acid. So, on average, about 1.4 grams of arachidonic acid is generated per day. When a patient consumes excessive amounts of PUFAs, including linoleic acid, that excess dilutes the effective concentration of 11,11-D2-linoleic acid. In turn, this impacts the amount of 13,13-D2-arachidonic acid that is hepatically generated when all other factors remain constant.

When the amount of total PUFAs consumed is such that the amount of 13,13-D2-arachidonic acid hepatically generated is less than about 70% per day of that generated when the average amount of PUFAs are consumed, then that patient is considered to have excessive linoleic acid consumption. Pathology The discovery of several aldehydes that easily reacted with sulfhydryl groups, resulting in the inhibition of vital metabolic processes, led to the association of polyunsaturated fatty acid peroxidation as a component of the pathology of many of neurodegenerative diseases (Schauenstein, E.; Esterbauer, H. Formation and properties of reactive aldehydes. Ciba Found. Symp. (67):225-244; 1978). Whether as a primary cause of disease or a secondary consequence, such lipid peroxidation is attributed to oxidative stress, which leads to neural death and this implicated in the progression of a number of neurodegenerative diseases. The oxidative stress responsible for such peroxidation is due to an imbalance between routine production and detoxification of reactive oxygen species ("ROS") that leads to an oxidative attack on the lipid membrane of cells. The lipid membrane as well as the endoplasmic reticulum and mitochondria of motor neurons are highly enriched in arachidonic acid (a 20-carbon chain polyunsaturated fatty acid ("PUFA") having 4 sites of cis-unsaturation). Separating each of these 4 sites are 3 bis-allylic methylene groups. These groups are particularly susceptible to oxidative damage due to ROS, and to enzymes such as cyclooxygenases, cytochromes and lipoxygenases, as compared to allylic methylene and methylene groups.

Moreover, once a bis-allylic methylene group in one arachidonic acid is oxidized by a ROS, a cascade of further oxidation of other arachidonic acid groups in the lipid membrane occurs. This is because a single ROS generates oxidation of a first arachidonic acid component through a free radical mechanism which, in turn, can oxidize a neighboring arachidonic acid through the same free radical mechanism which yet again can oxidize another neighboring arachidonic acid in a process referred to as lipid chain auto-oxidation. The resulting damage includes a significant number of oxidized arachidonic acid components in the cell membrane.

Oxidized arachidonic acids negatively affect the fluidity and permeability of cell membranes in motor neurons. In addition, they can lead to oxidation of membrane proteins as well as being converted into a large number of highly reactive carbonyl compounds. The latter include reactive species such as acrolein, malonic dialdehyde, glyoxal, methylglyoxal, etc. (Negre-Salvayre A, et al. Brit. J. Pharmacol. 2008; 153:6-20). But the most prominent products of arachidonic acid oxidation are alpha, beta-unsaturated aldehydes such as 4-hydroxynon-2-enal (4-HNE; formed from n-6 PUFAs like LA or AA), and corresponding ketoaldehydes (Esterfbauer H, et al. Free Rad. Biol. Med. 1991; 11:81-128. As noted above, these reactive carbonyls cross-link (bio) molecules through Michael addition or Schiff base formation pathways leading which continues the underlying pathology of the disease.

Disease Progression

When a patient is diagnosed with a specific neurodegenerative disease, the clinician evaluates that patient's rate of disease progression by assessing the patient's loss of functionality in the absence of therapy as described herein. That rate is referred to as the "natural history" of the disease and is typically measured by standardized tests that measure the extent of a patient's functionality over a set period of time. For example, in the case of ALS, there is a standard test referred to as ALSFRS-R which determines the rate of loss of muscle functionality over time and this is used to measure disease progression. This test has 12 components each of which are measured on a o (worse) to 4 (best) scale. The ability of a drug to attenuate the rate of disease progression evidences its efficacy. Even a modest reduction in the rate of functionality loss is considered significant.

Heretofore, the treatment of a variety of neurodegenerative diseases employed deuterated 11,11-D2-linoleic acid or an ester thereof, including those in a lipid bilayer form, to stabilize polyunsaturated fatty acids against ROS. Examples of such treatments are found in: ALS-WO 2011/053870, WO 2012/148946, and WO 2020/102596

Each of these documents discloses the in vivo hepatic conversion of a portion of 11,11-D2-linoleic acid to 13,13-D2-arachidonic acid which is then incorporated into the motor neurons to stabilize these neurons from oxidative damage. The in vivo accumulation of 13,13-D2-arachidonic acid occurs over weeks if not months until a therapeutic concentration is achieved. Once a therapeutic concentration of 13,13-D2-arachidonic acids is achieved, continued administration of 11,11-D2-linoleic acid or ester thereof is necessary to maintain such a therapeutic concentration.

Still further, the dosing regimen employed must address the patient's need for rapid onset of therapy especially given that loss of functionality is typically very quick and quite often well before the end stage of the disease which typically ranges from about 2 to 5 years after diagnosis. Hence, any therapy for treating such neurodegenerative diseases must provide meaningful therapy within a month or less after the start of therapy thereby retaining as much of the patient's functionality as possible and furthermore providing for substantial reductions in the rate of disease progression.

Compound Preparation

Deuterated linoleic acid such as 11,11-D2-linoleic acid and 8,8,11,11-D4-linoleic acid are known in the art and are commercially available. In addition, a variety of deuterated linoleic acids, including 11,11-D2-linoleic acid and esters thereof, are described, for example, in U.S. Pat. No. 10,052,299 which is incorporated herein by reference in its entirety. Esters of these deuterated fatty acids are prepared by conventional techniques well known in the art.

Methodology-11,11-D2-Linoleic Acid or Ester Thereof

The methods described herein utilize the hepatic conversion of linoleic acid to arachidonic acid by administering 11,11-D2-linoleic acid or an ester thereof to a patient in order to biosynthesize a therapeutic concentration of 13,13-D2-arachidonic acid for use in the methods described herein.

In one embodiment, 11,11-D2-linoleic acid or ester thereof is administered to the patient in sufficient amounts to generate a concentration of 13,13-D2-arachidonic acid in red blood cells of at least about 3%, preferably at least 5%, and more preferably at least 8%, based on the total amount of arachidonic acid, including deuterated arachidonic acid, found therein. At any of these concentrations, the attending clinician can correlate that concentration to a therapeutic concentration of 13,13-D2-arachidonic acid in the neurons. The percentage of 13,13-D2-arachidonic acid compared to total arachidonic acid in red blood cells may be between about 3% and about 60%. In an embodiment, the percentage of 13,13-D2-arachidonic acid compared to total arachidonic acid in red blood cells may be between about 3% and about 50%, between about 3% and about 40%, between about 3% and about 30%, between about 3% and about 20%, between about 3% and about 15%, between about 3% and about 10%, between about 3% and about 9%, or between about 3% and about 8%. In an embodiment, the percentage of 13,13-D2-arachidonic acid compared to total arachidonic acid in red blood cells may be between about 5% and about 50%, between about 5% and about 40%, between about 5% and about 30%, between about 5% and about 20%, between about 5% and about 15%, between about 5% and about 10%, or between about 5% and about 8%. In an embodiment, the percentage of 13,13-D2-arachidonic acid compared to total arachidonic acid in red blood cells may be between about 8% and about 50%, between about 8% and about 40%, between about 8% and about 30%, between about 8% and about 20%, between about 8% and about 15%, or between about 8% and about 10%. The percentage may be any value or subrange within the recited ranges, including endpoints.

In one embodiment, such administration comprises the use of a dosing regimen that includes two dosing components. The first dosing component comprises a primer dose of 11,11-D2-linoleic acid or an ester thereof. The second dosing component comprises a maintenance dose of 11,11-D2-linoleic acid or an ester thereof, wherein the amount of 11,11-D2-linoleic acid or an ester thereof in said second dosing component is less than that in the first dosing component.

As to the primer dose, the amount of 11,11-D2-linoleic acid or an ester thereof employed is designed to provide rapid onset of therapy. Such therapy is measured by a reduction in the disease progression of neurodegenerative diseases as described below. In an embodiment, the primer dose takes into account the various complicating factors, such as the amount of PUFAs consumed by the patient in a given day, the in vivo rate of conversion of 11,11-D2-linoleic acid to 13,13-D2-arachidonic acid, as well as the general turnover rate of lipids (half-life) in the patient's neurons.

Regarding this last point, the lipid components of neurons are not static but, rather, are exchanged over time and have a finite half-life in the body. In general, only a fraction of the lipids components in the lipids are replaced each day. In the case of neurons, these cells are rich in arachidonic acid. The turnover of arachidonic acid in these membranes occurs from a stable pool of lipids comprising arachidonic acid in the spinal fluid. In turn, this stable pool is replaced and replenished over time by arachidonic acid included in the newly consumed lipids by the patient as part of the patient's diet as well as by biosynthesis of arachidonic acid from linoleic acid by the liver. In embodiments, the maintenance dose of the 11,11-D2-linoleic acid is titrated such that the amount converted to 13,13-D2-arachidonic acid matches the rate of secretion from the body.

The rate of arachidonic acid synthesized by the liver is typically rate limited to the extent that there is a maximum amount of arachidonic acid that the liver can generate in a given day. In turn, only a fraction of the linoleic acid consumed is converted to arachidonic acid with the majority of the linoleic acid remaining unchanged. This limited rate of hepatic synthesis of arachidonic acid from linoleic acid results in a delay in such synthesis after administration of the deuterated linoleic acid as the amount of 13,13-D2-arachidonic acid concentration in red blood cells continues to increase after converting from the primer dose to the maintenance dose of the dosing regimen. This increase is contra-suggested, as the maintenance dose employs less 11,11-D2-linoleic acid as compared to the primer dose. However, without being limited to any theory, we believe that this increase is due to a lag in the hepatic conversion of 11,11-D2-linoleic acid to 13,13-D2-arachidonic acid after the administration of 11,11-D2-linoleic acid.

Hence, the choice of a dosing of 11,11-D2-linoleic acid as described herein addresses each of the above components and sets a dosing level that allows for the accumulation of a sufficient amount of 11,11-D2-linoleic acid in the body and, hence, the generation of therapeutic levels of 13,13-D2-arachidonic acid in the red blood cells. When so achieved, the data in the Examples establish that there is a significant reduction in the rate of disease progression.

In embodiments, the loading dose of the dosing regimen described herein includes sufficient amounts of 11,11-D2-linoleic acid that are absorbed into the patient so as to maximize the in vivo conversion of 11,11-D2-linoleic acid 13,13-D2-arachidonic acid. Once maximized, the resulting 13,13-D2-arachidonic acid accumulates in the body until it reaches a therapeutic concentration in the patient. During this process, 13,13-D2-arachidonic acid is systemically absorbed into the cells of the body including neurons, wherein the rate at which such absorption occurs is based on the exchange rate or turnover rate of lipids in the cell membrane of these motor neurons.

This disclosure is based on the discovery that given the above variables, the amount of 11,11-D2-linoleic acid or ester thereof that is administered over time and converted in vivo to 13,13-D2-arachidonic acid is selected so that the fatty acids contained in red blood cells comprise at least about 3% and preferably at least about 5%, and more preferably, at least about 8% of 13,13-D2-arachidonic acid when tested at one (1) month after the start of therapy. At that level, the deuterated arachidonic acid concentration stabilizes the cell membrane and limits or prevents the cascade of lipid auto-oxidation. When so administered, there is a significant reduction in the progression rate of the neurodegenerative disease being treated.

The methods described herein are also based, in part, on the discovery that when the lipid membrane of neurons is stabilized against LPO, there is a substantial reduction in the progression of the neurodegenerative disease. This is believed to be due to the replacement of hydrogen atoms with deuterium atoms at the 13,13-bis-allylic positions of arachidonic acid, rendering the deuterated arachidonic acid significantly more stable to ROS than the hydrogen atoms. As above, this stability manifests itself in reducing the cascade of lipid auto-oxidation and, hence, limiting the rate of disease progression.

In the specific instance of ALS, the reduction in the progression of this disease can be readily calculated by using the known and established rate functional decline measured by the R-ALS Functional Rating Scale-revised after commencement of drug therapy as compared to the rate of decline prior to drug therapy (natural history of decline). As the rate of decline is not perceptible on a day-to-day basis, the functional decline is typically measured monthly and is evaluated over a period of time such as every 1 to 24 months, such as every 3 months, every 6 months, or annually.

As set forth in the examples below, the rate of functional decline is predicated on measuring an individual's, or a cohort's, average for the natural history of disease progression. Next, the individual or cohort average for the functional decline is determined at a period of time such as at 3, 6 or 12 months after initiation of therapy. The rate of decline based on the average of the natural history of the cohort is set as the denominator. The numerator is set as the delta between the rate of the natural history of disease progression and the rate of functional decline after a set period of treatment per this invention. The resulting fraction is the multiplied by 100 to give a percent change. The following exemplifies this analysis.

Cohort A has an average natural history rate of decline in functionality of 28 annualized for a one (1) year period. Six (6) months after initiation of treatment per this invention, Cohort A an annualized average rate of decline in functionality has dropped to 14. This provides a delta of 14 degrees. So, using 14 as the numerator and 28 as the denominator and then multiplying result by 100, one obtains a reduction in the annualized rate of decline of 50 percent.

In general, the methods of this invention provide for an average percent change in reduction in functionality for a cohort of at least 30% and, more preferably, at least about 35%, or at least about 40%, or at least about 45%, or at least about 50%, or at least about 55%, or at least about 60%. In embodiments, the change in reduction of functionality is measured over a time period, for example 1 month to 24 months, e.g, at 3 months, at 6 months, or annually. The rate of decline can be measured over any time period intermediate between 3 months and 1 year.

The dosing regimen employed is predicated on numerous factors such as the rate of hepatic conversion of 11,11-D2-linoleic acid to 13,13-D2-arachidonic acid, and whether the deuterated linoleic acid (including esters) are properly absorbed into the body. This, in turn, is controlled by the overall intake of all of the polyunsaturated fatty acids (PUFAs) consumed by the patient. Not all of the daily PUFAs consumed by a patient are absorbed by the body. Rather, the amount absorbed is predicated on several factors including the patient's metabolism and the total amount of PUFAs consumed per day by the patient. Still further, as to linoleic acid, only a portion of linoleic acid so absorbed is converted to arachidonic acid.

These variable functions in the amount of deuterated linoleic acid consumed and actually absorbed by the body pose a challenge to the dosing regimen. Moreover, it is preferable that the dosing regimen also address the challenge of providing for a dosing regimen that allows for rapid onset to quickly reduce the rate of disease progression in the patient so as to minimize the additional loss of functionality and then to maintain such a reduced rate. It is to be understood that reducing the rate of disease progression correlates to longer periods of retained functionality in the patient and likely a longer lifespan. Accordingly, the faster one reaches such a reduced rate, the better off it is for the patient.

In one embodiment, the methods described herein address this challenge by employing a dosing regimen which delivers 11,11-D2-linoleic acid in amounts sufficient to provide for a therapeutic amount of deuterated arachidonic acid in the neurons. When so incorporated, the deuterated arachidonic acid reduces the degree of LPO which, in turn, effectively limits progression of ALS provided it is administered in appropriate amounts.

Combinations

The therapy provided herein can be combined with conventional treatment of used with neurodegenerative diseases provided that such therapy is operating on an orthogonal mechanism of action relative to inhibition of lipid auto-oxidation. Suitable drugs for use in combination include, but not limited to, antioxidants such as edaravone, idebenone, mitoquinone, mitoquinol, vitamin C, or vitamin E provided that none of these anti-oxidants that are directed to inhibiting lipid auto-oxidation, riluzole which preferentially blocks TTX-sensitive sodium channels, conventional pain relief mediations, and the like.

Pharmaceutical Compositions

The specific dosing of 11,11-D2-linoleic acid or an ester thereof is accomplished by any number of the accepted modes of administration. As noted above, the actual amount of the drug used in a daily or periodic dose per the methods of this invention, i.e., the active ingredient, is described in detail above. The drug can be administered at least once a day, preferably once or twice or three times a day.

This invention is not limited to any particular composition or pharmaceutical carrier, as such may vary. In general, compounds of this invention will be administered as pharmaceutical compositions by any of a number of known routes of administration. However, orally delivery is preferred typically using tablets, pills, capsules, and the like. The particular form used for oral delivery is not critical but due to the large amount of drug to be administered, a daily or periodic unit dose is preferably divided into subunits having a number of tablets, pills, capsules, and the like. In one particularly preferred embodiment, each subunit of the daily or periodic unit dose contains about I gram of the drug. So, a daily or periodic unit dose of 9 grams of the drug is preferably provided as 9 sub-unit doses containing about I gram of the drug. Preferably, the unit dose is taken in one, two or three settings but, if patient compliance is enhanced by taking the daily or periodic unit dose over 2 or 3 settings per day, such is also acceptable.

Pharmaceutical dosage forms of a compound as disclosed herein may be manufactured by any of the methods well-known in the art, such as, by conventional mixing, tableting, encapsulating, and the like. The compositions as disclosed herein can include one or more physiologically acceptable inactive ingredients that facilitate processing of active molecules into preparations for pharmaceutical use.

The compositions can comprise the drug in combination with at least one pharmaceutically acceptable excipient. Acceptable excipients are non-toxic, aid administration, and do not adversely affect the therapeutic benefit of the claimed compounds. Such excipient may be any solid, liquid, or semi-solid that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Other suitable pharmaceutical excipients and their formulations are described in Remington's Pharmaceutical Sciences, edited by E. W. Martin (Mack Publishing Company, 18th ed., 1990).

The compositions as disclosed herein may, if desired, be presented in a pack or dispenser device each containing a daily or periodic unit dosage containing the drug in the required number of subunits. Such a pack or device may, for example, comprise metal or plastic foil, such as a blister pack, a vial, or any other type of containment. The pack or dispenser device may be accompanied by instructions for administration including, for example, instructions to take all of the subunits constituting the daily or periodic dose contained therein.

The amount of the drug in a formulation can vary depending on the number of subunits required for the daily or periodic dose of the drug. Typically, the formulation will contain, on a weight percent (wt %) basis, from about 10 to 99 weight percent of the drug based on the total formulation, with the balance being one or more suitable pharmaceutical excipients. Preferably, the compound is present at a level of about 50 to 99 weight percent.

In preferred embodiment, the drug is encapsulated inside a capsule without the need for any pharmaceutical excipients such as stabilizers, antioxidants, colorants, etc. This minimizes the number of capsules required per day by maximizing the volume of drug in each capsule.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention.

Various modifications of this invention in addition to those described herein will become apparent to those skilled in the art from the foregoing description and accompanying figures. Such modifications fall within the scope of the appended claims. In these examples, the following terms are used herein and have the following meanings. If not defined, the abbreviation has its conventional medical meaning.

D2-AA AA 13,13-D2-Arachidonic Acid Arachidonic Acid

ALSFRS-R CNS Revised ALS Functional Rating Scale Central

CSF D2-LA Nervous System

LA PK RBC Cerebral Spinal Fluid

SAE 11,11-D2-Linoleic Acid (aka "drug") Linoleic Acid

Pharmacokinetics Red

Blood Cells

Serious Adverse Events

Example 1-Determination of AA Concentrations in RBCs and Spinal Fluid/Neurons in a Single Patient This example determines the relative concentration of D2-AA in the CSF and in RBCs in order to determine if there is a correlation between these two concentrations. Specifically, a patient was continuously provided with a daily dose of 9 grams of D2-LA ethyl ester over about a six-month period. Periodic samples of blood and SF were taken and the concentration of both D2-LA and D-2AA in both the RBCs and the SF were measured. In all cases, the D2-AA was obtained by deacylation of the ethyl ester of linoleic acid in the gastrointestinal tract followed by hepatic conversion of D2-LA in vivo to D2-AA.

TABLE 1

| Time | Concentration of D2-LA in SF | Concentration of D2-AA in SF | Ratio of D2-LA to D2-AA in SF |
|---|---|---|---|
| 1 month | 19.8% | 8% | 2.5:1 |

The results found in Table 1 show that the concentration of D2-AA in the cerebral spinal fluid is already 8% based on the amount of arachidonic acid+deuterated arachidonic acid. Next, Table 2 shows that the concentration of D2-LA and D2-AA in the RBCs at 3 months and 6 months for the same patient.

TABLE 2

| Time | Concentration of D2-LA in RBCs | Concentration of D2-AA in RBCs | Ratio of D2-LA to D2-AA in RBCs |
|---|---|---|---|
| 3 months | 34.7% | 11.8% | 2.9:1 |
| 6 months | 34.5 | 16.7 | 2.1:1 |

Note here that the concentration of D2-AA in RBC's at 3 months is less than that at 6 months evidencing the incremental increase in D2-AA over time. Moreover, the ratio of D2-LA to D2-AA changes from 2.9:1 at 3 months to 2.1:1 at 6 months. In one embodiment, the ratio of D2-LA to D2-AA in RBCs at 3 and 6 months is represented as 2.5:1+/−0.4 which corresponds favorably to that found in Table 1.

Since the amount of D2-AA is increasing over time in an incremental fashion based on the hepatic conversion of D2-LA, one can assume a fairly linear rate of increase. This is shown in FIG. 1, where the solid line is set by the concentrations of D2-AA at 3 months and 6 months and then extrapolated back to start of therapy (0 months). The value for the D2-AA in RBC's at I month is estimated from this relationship. The amount shown for I month in the CSF is also provided (open circle).

Based on the above, one can see that the data to date suggests that the amount D2-AA at I month in RBCs would be about 3 percent as compared to 8% for the amount of D2-AA in the SF. Accordingly, this data suggests that the concentration the body shunts more of the AA (including D2-AA) into the CSF (and hence the neurons) as compared to RBCs and likely other reporter cells.

Example 2-Determination of AA Concentrations in RBCs and Spinal Fluid/Neurons in a Cohort of 14 Patients In this example, children suffering from INAD were treated with a daily dose of 3 grams of D2-LA ethyl ester followed by 2 grams of D2-LA ethyl ester. Given the age and weight of these children, such is assumed to be substantially equivalent to between about 7 and about 12 grams per day for an adult patient.

This example also determines the concentration of D2-AA in RBCs. Specifically, a cohort of 14 children was provided with a daily dose of 3 grams of D2-LA ethyl ester for I month followed by 2 grams of D2-LA ethyl ester for the remaining six-month period. Blood samples were taken at 3 months for all but I child and at 6 months for all children. The concentration of D2-AA in RBCs was measured. In all cases, the D2-AA was obtained by deacylation of the ethyl ester of linoleic acid in the gastrointestinal tract followed by hepatic conversion of D2-LA in vivo to D2-AA.

At 3 months, the average concentration of D2-AA in the RBCs was determined to be 12% (6.8% low and 16.8% high). At 6 months, the average concentration of D2-AA in the RBCs was determined to be 16.7% (12.0% low and 26.1% high). A graph depicting these results is provided as FIG. 2. The line shows a linear relationship of D2-AA accumulation in the body. Included in this graph is the I-month data for D2-AA in the spinal fluid as found in Example 1.

Figure 2:
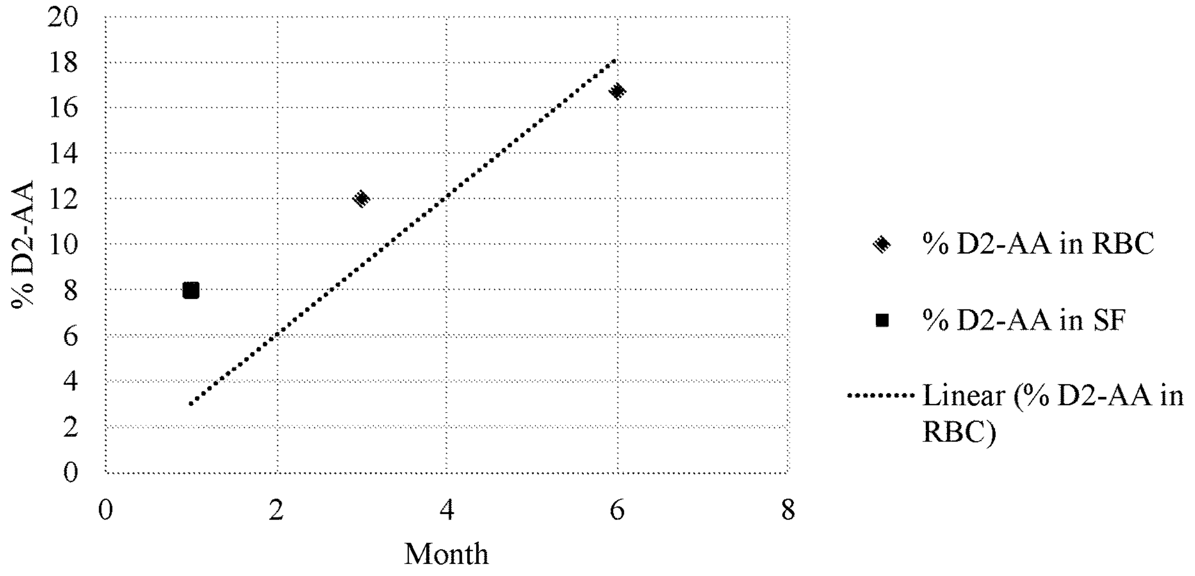
FIG. 2 is a graph showing the percent of 13,13-D2-Arachidonic Acid in red blood cells (RBC) and spinal fluid (SF) at the indicated time points after start of treatment with 11,11-D2-Linoleic Acid in juvenile patients.

As can be seen, the graphs in FIGS. 1 and 2 are substantially the same, strongly suggesting that the dosing of D2-LA to the adult patient in Example I and to the children in Example 2 maximized the hepatic conversion of D2-LA to D2-AA. This data further suggests that once maximized, the amounts of D2-AA generated over time are reproducible.

Comparative Example A

Patients suffering from ALS were treated with D2-LA over a period of time. The patients were given different dosing amounts of D2-LA and for different dosing periods but did not follow the dosing protocol described herein. Some patients were provided 2 grams of 11,11-D-2 LA per day as opposed to the loading dose of 9 grams per day.

Functional scores for each of the patients (ALSFRS-R results) at the end of therapy were compared to the natural history scores at the start of therapy. Based on this comparison, the rate of decline changed from an annualized rate of −14.2+/−4.4 per year pre-treatment to −7.6+/−1.4 during treatment or a 46% reduction (p=0.07, paired t-test for within-subject change in slope).

Example 3—Benefits of the Dosing Protocol

This example illustrates the reduction in the rate of disease progression in patients with ALS treated by the dosing methods described herein. Specifically, a cohort of 3 patients was placed on a dosing regimen consisting of a first dosing component (primer dose) of about 9 grams of D2-LA ethyl ester daily for a period of at least 30 days and then all three patients were transitioned to a second dosing component (maintenance dose) of 5 grams of D2-LA ethyl ester.

The functionality of each of the patients was evaluated periodically using the ALSFRS-R protocol. The patients continued on the dosing regimen for a period of 6 months (patient A) or 1 year (patient B) or for 9 months (patient C). Patient C died at the end of 9 months and his death was attributed to factors other than ALS cardiomyopathy. Before initiation of therapy, the natural history of each patient in the cohort was determined and an average annual rate of functional decline was measured at 21.

The annualized progression of the disease as measured by an average annual rate of functional decline for all three patients starting at the time that dosing began and terminating at the end of the dosing regimen and then annualized as described above was measured as 2.1. Using the formula described above, one obtains the following:

(21−2.1)/21×100=90% annualized average reduction in the rate of disease progression.

The specific values for each of the three members of the cohort are as follows in Table 5:

TABLE 5

| Patient | NH Rate of Decline | Functional Rate Decline During Therapy |
|---|---|---|
| A | −16 | −3 |
| B | −31 | −2 |
| C | −16 | −1.3 |

NH = Natural History

These results substantiate a very significant rate of reduction in the disease progression using the dosing regimen as per this invention. These results also substantiate that transitioning patients from a primer dose to a maintenance dose maintains the beneficial stabilization in the rate of decline.

In comparison, patients treated with 9 gm of D2-LA per day for about 1 month followed by 5 gm of D2-LA per day thereafter evidence about a 90% reduction in the rate of disease progression. Compared to the 46% rate of reduction in the This establishes that the dosing regimen described herein provides for a significant benefit to patients in their reduction in the rate of disease progression.

The invention claimed is:

1. A method for reducing disease progression of a neurodegenerative disease treatable with 11,11-D2-linoleic acid in a patient, comprising:

administering 11,11-D2-linoleic acid or an ester thereof to the patient with a dosing regimen that comprises a primer dose and a maintenance dose thereby reducing the disease progression in the patient, wherein:

a) the primer dose comprises periodic administration of from about 7 to 12 grams of 11,11-D2-linoleic acid or an ester thereof per day, wherein the primer dose is continued for about 30 days to about 45 days to rapidly achieve a therapeutic concentration of 13,13-D2-arachidonic acid in vivo; and b) subsequent to completion of the primer dose, periodically administering the maintenance dose of no more than about 65% of the primer dose of 11,11-D2-linoleic acid or an ester thereof per day thereof to maintain the therapeutic concentration of 13,13-D2-arachidonic acid in vivo, such that a rate of disease progression is reduced, wherein the neurodegenerative disease is mediated at least in part by lipid peroxidation of polyunsaturated fatty acids in neurons of the patient;

wherein the disease is amyotrophic lateral sclerosis, Huntington's Disease, progressive supranuclear palsy (PSP), Friedreich's ataxia, APO-e4 Alzheimer's Disease, corticobasal disorder (CBD), frontotemporal dementia (FTD), nonfluent variant primary progressive aphasia (nfvPPA), other tauopathies, and late onset Tay-Sachs.

2. The method of claim 1, wherein the periodic administration of the primer dose comprises administration of about 9 grams of 11,11-D2-linoleic acid or an ester thereof per day for at least 5 days per week.

3. The method of claim 1, wherein the periodic administration of the primer dose comprises administration of about 9 grams of 11,11-D2-linoleic acid or a C1-C6 alkyl ester thereof per day for each day.

4. The method of claim 1, wherein the periodic administration of the maintenance dose comprises no more than 55% of the primer dose which is administered at least once a month.

5. The method of claim 4, wherein the periodic administration of the maintenance dose comprises no more than 35% of the primer dose which is administered at least once a week.

6. The method of claim 5, wherein the periodic administration of the maintenance dose is calibrated to be an amount of 11,11-D2-linoleic acid or an ester thereof sufficient to replace the amount of 13,13-D2-arachidonic acid removed by conversion of a portion of 11,11-D2-linoleic acid to 13,13-D2-arachidonic acid.

7. The method of claim 6, wherein the periodic administration of the maintenance dose comprises is administered at least once a month.

8. The method of claim 1, wherein a percent reduction in the rate of disease progression is determined by:

measuring a natural rate of disease progression in a patient or an average natural rate of disease progression in a cohort of patients;

measuring the rate of disease progression in the patient or cohort of patients during a period of compliance with the administering; and after 1 month or 3 months since the onset of therapy, calculating the difference between the natural rate and a rate during the period of compliance, dividing the difference by the rate of disease progression during the natural history of the patient, and multiplying by 100.

9. The method of claim 1, which further comprises restricting the the patient from consuming excessive dietary polyunsaturated fatty acids during administration of the primer and the maintenance doses.

10. The method of claim 1, wherein the primer dose and/or the maintenance dose is provided in 1, 2 or 3 administrations during a single day.

11. The method of claim 1, wherein the neurodegenerative disease is amyotrophic lateral sclerosis, Huntington's Disease, progressive supranuclear palsy (PSP), Friedreich's ataxia, or APO-e4 Alzheimer's Disease.

* * * * *